US008070716B2

(12) United States Patent
Sutrina et al.

(10) Patent No.: US 8,070,716 B2
(45) Date of Patent: *Dec. 6, 2011

(54) METHOD AND APPARATUS FOR MINIMUM NEGATIVE PRESSURE CONTROL, PARTICULARLY FOR A BREASTPUMP WITH BREASTSHIELD PRESSURE CONTROL SYSTEM

(75) Inventors: Thomas A. Sutrina, Rockford, IL (US); Michael Dettling, Woodstock, IL (US); Mark A. Luzbetak, Kildeer, IL (US); Brian H. Silver, Cary, IL (US); Carr Lane Quackenbush, Prairie Grove, IL (US); Leon R. Mitoulas, Cham (CH); Peter E. Hartmann, Gooseberry Hill (AU); Donna T. Geddes, Dianella (AU); Jacqueline C. Kent, Nedlands (AU)

(73) Assignee: Medela Holding AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/248,686

(22) Filed: Oct. 9, 2008

(65) Prior Publication Data
US 2009/0099511 A1    Apr. 16, 2009

Related U.S. Application Data

(63) Continuation-in-part of application No. 11/786,364, filed on Apr. 11, 2007.

(51) Int. Cl.
*A61M 1/06* (2006.01)
(52) U.S. Cl. ............................................. 604/74; 604/73
(58) Field of Classification Search .................... 604/35, 604/36, 73–76, 132, 133, 346; 417/36–38
See application file for complete search history.

(56) References Cited

U.S. PATENT DOCUMENTS

| 3,159,176 A | 12/1964 | Russell et al. |
| 4,213,457 A | 7/1980 | Lewis |
| 4,315,506 A | 2/1982 | Kayser et al. |
| 4,607,596 A | 8/1986 | Whittlestone et al. |
| 4,671,209 A | 6/1987 | Whittlestone et al. |
| 4,794,915 A | 1/1989 | Larsson |
| 4,857,051 A | 8/1989 | Larsson |
| 4,883,464 A | 11/1989 | Morifuki |

(Continued)

FOREIGN PATENT DOCUMENTS

CA    2530726    6/2006

(Continued)

OTHER PUBLICATIONS

International Search Report for corresponding PCT Application No. PCT/US2009/059768 mailed Feb. 15, 2010 (4 pages).

(Continued)

*Primary Examiner* — Nicholas Lucchesi
*Assistant Examiner* — Nathan R Price
(74) *Attorney, Agent, or Firm* — McDonnell Boehnen Hulbert & Berghoff LLP

(57) ABSTRACT

A breastpump, manual or motorized, that includes a mechanism to regulate pressure change, e.g., vacuum, within a breastshield chamber, including in some cases to a maintained minimum pressure that is less than ambient (atmosphere). The pressure regulator provides control for varying negative pressure between a minimum value and a maximum value (and values in between), or to achieve a specific actually measured negative pressure value within a breastshield.

65 Claims, 15 Drawing Sheets

U.S. PATENT DOCUMENTS

| | | | |
|---|---|---|---|
| 4,929,229 A * | 5/1990 | Larsson | 604/74 |
| 4,964,851 A | 10/1990 | Larsson | |
| 5,007,899 A | 4/1991 | Larsson | |
| 5,295,957 A | 3/1994 | Aida et al. | |
| 5,373,972 A | 12/1994 | Bystrom et al. | |
| 5,514,166 A | 5/1996 | Silver et al. | |
| 5,601,531 A | 2/1997 | Silver | |
| 5,797,875 A | 8/1998 | Silver | |
| 5,860,388 A | 1/1999 | Tan et al. | |
| 5,902,267 A | 5/1999 | Medo | |
| 5,941,847 A | 8/1999 | Huber et al. | |
| 6,045,529 A | 4/2000 | Nuesch | |
| 6,110,140 A | 8/2000 | Silver | |
| 6,139,521 A | 10/2000 | Larsson | |
| 6,299,594 B1 | 10/2001 | Silver | |
| 6,383,163 B1 | 5/2002 | Kelly et al. | |
| 6,461,324 B1 * | 10/2002 | Schlensog | 604/74 |
| 6,497,677 B2 | 12/2002 | Silver | |
| 6,547,756 B1 | 4/2003 | Greter et al. | |
| 6,652,484 B1 | 11/2003 | Hunckler et al. | |
| 6,663,587 B2 | 12/2003 | Silver et al. | |
| 6,676,631 B1 | 1/2004 | Greter | |
| 6,699,213 B1 | 3/2004 | Annis et al. | |
| 6,706,012 B2 | 3/2004 | McKendry et al. | |
| 6,749,582 B2 | 6/2004 | Britto et al. | |
| 7,029,454 B2 | 4/2006 | Watanabe | |
| 7,166,087 B2 | 1/2007 | Silver et al. | |
| 7,727,182 B2 | 6/2010 | Silver | |
| 2002/0193731 A1 | 12/2002 | Myers et al. | |
| 2004/0024351 A1 | 2/2004 | Greter et al. | |
| 2004/0039330 A1 | 2/2004 | Silver | |
| 2005/0043677 A1 | 2/2005 | Kelly et al. | |
| 2005/0159701 A1 * | 7/2005 | Conaway | 604/74 |
| 2005/0214129 A1 | 9/2005 | Greene et al. | |
| 2005/0222536 A1 | 10/2005 | Silver | |
| 2005/0228342 A1 | 10/2005 | Yuen | |
| 2005/0234370 A1 | 10/2005 | Beal et al. | |
| 2006/0052746 A1 | 3/2006 | Liao | |
| 2008/0171970 A1 | 7/2008 | Luzbetak et al. | |
| 2008/0177224 A1 | 7/2008 | Kelly et al. | |

FOREIGN PATENT DOCUMENTS

| | | |
|---|---|---|
| EP | 1468705 | 10/2004 |
| JP | 2002035111 | 2/2002 |
| JP | 2004000486 | 1/2004 |
| WO | WO01/47577 | 7/2001 |
| WO | WO2005/016409 | 2/2005 |
| WO | 2008/127991 | 10/2008 |

OTHER PUBLICATIONS

International Search Report dated Sep. 16, 2008 issued in related International Appl. No. PCT/US08/59927 (2 pages).

Kent, J.C., et al., "Response of Breasts to Different Stimulation Patterns of an Electric Breast Pump," Journal of Human Lactation, vol. 19, No. 2, pp. 179-186, 2003.

Mitoulas, L.R., et al., "Efficiency of Breast Milk Expression Using an Electric Breast Pump," Journal of Human Lactation, vol. 18, No. 4, pp. 344-352, 2002. See whole document.

Mitoulas, L.R., et al., "Effect of Vacuum Profile on Breast Milk Expression Using an Electric Breast Pump," Journal of Human Lactation, vol. 18, pp. 353-360, 2002. See whole document.

International Search Report for Application PCT/AU2007/001402 issued Nov. 8, 2007.

International Search Report for Application PCT/AU2007/001401 issued Oct. 30, 2007.

510(k) filing for Limerick, inc. for pj's comfort jr.® Portable Electric Breast Pump, dated Dec. 12, 2005.

* cited by examiner

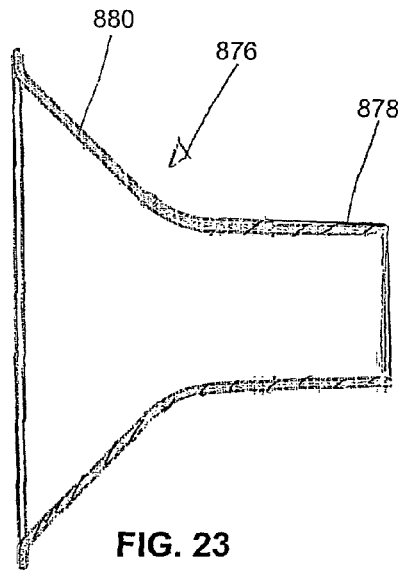
FIG. 23
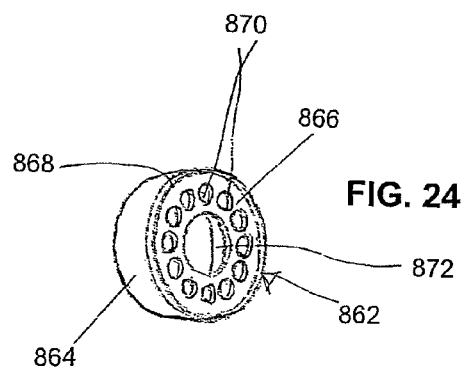
FIG. 24
FIG. 26
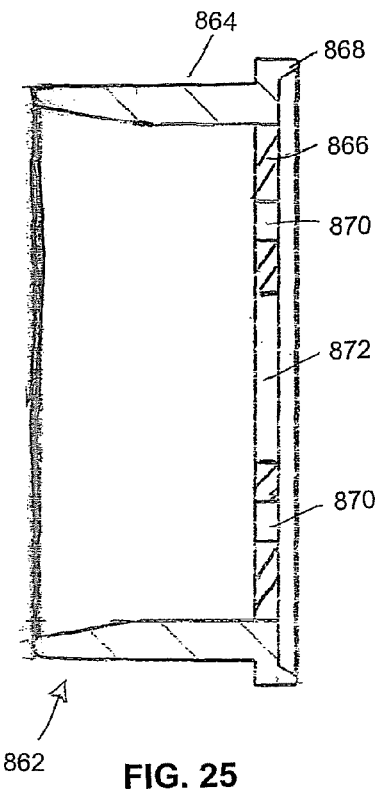
FIG. 25
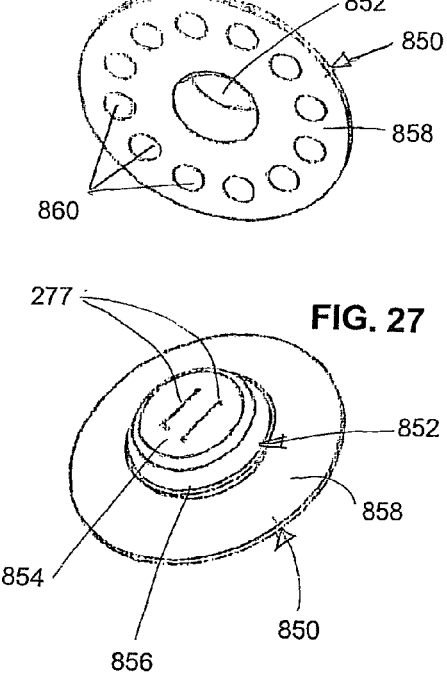
FIG. 27

METHOD AND APPARATUS FOR MINIMUM NEGATIVE PRESSURE CONTROL, PARTICULARLY FOR A BREASTPUMP WITH BREASTSHIELD PRESSURE CONTROL SYSTEM

FIELD OF THE INVENTION

This application is a continuation-in-part of application Ser. No. 11/786,364 filed on Apr. 11, 2007 entitled "Method and Apparatus for Minimum Negative Pressure Control, Particularly for Breastpump with Breastshield Pressure Control System."

This invention relates to breastpumps for drawing breastmilk, and particularly to a breastpump whether operated manually or motorized, with a pressure control system to regulate the pressure as actually applied to the breast within a breastshield chamber during a pumping cycle, and also to vary that pressure in a cycle that maintains a minimum vacuum.

BACKGROUND OF THE INVENTION

Breastpumps for use by nursing mothers are well known. They allow the nursing woman to express the breastmilk as necessary or convenient, and further provide collection of the breastmilk for later use. For some mothers, breastpumps may be a necessity, such as when the child has suckling problems, or if the mother has problems with excessive or deficient milk production, or soreness, deformation or injury of the mammilla, or like conditions that are not conducive to suckling at the breast.

There are three general broad classifications of breastpumps: hand pumps that generate suction manually, battery operated pumps with small motors that generate suction from power supplied by batteries, and electric pumps in which suction is created by various types of electric motors that run off "house" current. Some pumps can cross over these broad classifications.

Various types of hand pumps exist. An example of such manually-driven pumps is in U.S. Pat. No. 6,497,677.

A battery-driven portable breastpump is described in U.S. Pat. No. 4,964,851, for example. This breastpump is small, lightweight and achieves good vacuum (i.e., negative pressure) regulation in preferred limits. The LACTINA breastpump sold by Medela, Inc. is also another type of breastpump, which may be driven by battery as well as house current. It is generally disclosed in U.S. Pat. No. 5,007,899.

All of these breastpumps are designed to cycle pressure, typically a negative pressure or vacuum, that is applied to the breast and nipple within the breastshield. Conventional breastpumps are generally of the displacement pump type or accumulator pump type. Displacement pumps use a mechanism to expand a volume to thereby generate a vacuum, such as the foregoing piston-type pumps. At the end of the return stroke, they return to atmosphere. A maximum (or other) vacuum is achieved by the length of the stroke. Upon returning the breast shield to atmospheric pressure, a one way valve may be opened to discharge accumulated leakage air, excess air from the repositioning of the breast tissue, and expelled milk within the breast shield. The discharge occurs into an atmosphere vented milk collection bottle or flexible bag. Alternatively, air can be adjustably added during a fixed-length stroke (as by an adjustable return to atmosphere) to roughly establish a desired vacuum level.

Accumulator pumps build up vacuum by repeatedly exhausting small portions of the original quantity of gas in the system. As the amount of gas (air) in a fixed volume decreases, the pressure decreases causing the vacuum to increase. Accumulator pumps control the maximum vacuum via the time, or duration, the pump is powered on and operating, e.g., the number of pump reciprocations for a given cycle. Vacuum can also be adjusted via a regulator, like that of the battery-driven portable breastpump described in U.S. Pat. No. 4,964,851, for example.

An issue with conventional breastpumps is that the "system" volume within the breastshield varies due to the amount of volume the breast of a nursing mother occupies in the breastshield, as well as the response of a given breast under vacuum. For example, a nursing mother with engorged breasts will have tight breast and nipple tissue that may occupy the breastshield differently from a mother with highly elastic breast tissue and/or nipples. So too, a small breast or nipple may fill the breastshield and react differently from a large breast or nipple. The system volume thus varies from breast to breast, and even from time to time for the same breast.

This "variable system volume," sometimes referred to as the "dead" volume, is problematic within a suction cycle. Imagine a highly elastic breast/nipple; at the start of the suction cycle, the breast and nipple occupy a certain portion of the breastshield system volume. This fixes the starting quantity of air in the system. As suction builds, the breast/nipple tissue is drawn into the breastshield, partially relieving the buildup of vacuum. Thus, the developed vacuum within the cycle is less than would be realized with a less elastic breast/nipple.

To the extent that conventional breastpumps of the displacement or accumulator types have attempted to provide actual set points for vacuum desired, they do so only through an approximation. A vacuum setting of "250 mmHg" for such pumps would only be for a standard sized breast for example, since it is based upon an expected level derived from displacement, or alternatively accumulation, effected by operation. The method or mechanism by which a vacuum is regulated is thus not controlled by the actual pressure sensed at the breast.

Some prior art patents disclose regulating pressure with a sensed pressure. U.S. Pat. No. 5,902,267 to Medo discloses a regulator within a central vacuum system that applies the regulated output to a pump "flange" on the breast, and then returns to ambient pressure in a cycle.

U.S. Pat. No. 6,383,163 to Kelly discloses a vacuum sensor for sensing suction in the breast cup and opening a valve when a maximum suction is sensed to release the pressure and return the breast cup to ambient. Upon the breast cup achieving ambient pressure, the valve closes for another cycle.

Unlike the present invention, the prior art does not regulate vacuum at the breastshield to reach a maximum negative pressure, and then a desired minimum negative pressure still less than ambient, without the need to return to atmospheric pressure for successful milk expression. A return to ambient pressure within the breastshield chamber may not be required, and benefits may be achieved by maintaining a minimum level of vacuum on the breast throughout at least a portion of the pumping session. Such would include, for example, reducing the amount of energy required to thereafter reach maximum vacuum. The "elastic rebound" of the nipple upon release of vacuum would also be minimized. Further benefits may result from being able to control a given vacuum cycle between desired set points of actually sensed, and thereby actually applied pressures, which set points may be made numerous for more complex, yet precisely controlled suction curves. The present invention also provides comfort to the nursing mother in that the reciprocation of a breast or nipple within the breastshield is minimized.

Patent application Ser. No. 11/786,364 entitled "Method and Apparatus for Minimum Negative Pressure Control, Particularly for Breastpump with Breastshield Pressure Control System," describes means of using an accumulator breast pump with sensors to control the vacuum cycle precisely including the minimum vacuum. The application describes a breast shield which, when in contact with a breast, has internal pressure controlled by the control system, and where the internal breast shield pressure communicates with the milk collection bottle to bring the bottle to the minimum vacuum. Some slight cyclic variation to greater vacuum occurs each pumping cycle within the bottle collection. The collection bottle is sealed from the atmosphere. Opening of the one way valve is assisted by the higher vacuum in the bottle as the breast shield approaches the minimum vacuum, a lower vacuum.

SUMMARY OF THE INVENTION

It is a principal objective of the present invention to provide a breastpump, either manual or motorized, that includes a mechanism that can be used to regulate pressure change, e.g., vacuum, within a breastshield chamber, and even fairly precisely regulate that pressure in one preferred form.

The present invention in another significant aspect operates a pumping cycle that maintains a minimum level of vacuum within a breastshield chamber throughout at least some, if not all, of a pumping session. A desired minimum level can be attained such that a nipple does not achieve a relaxed state. A minimum vacuum in the range of about 20 mmHg to about 60 mmHg is presently considered most desirable, although about 15 mmHg is also considered desirable.

In an embodiment, a regulator used in conjunction with a motorized pump that regulates vacuum within a breastshield chamber operates according to a controller and actual sensed vacuum to the breast, with preset instructions or user input parameters, and may automatically transition between different operating conditions according to the preset instructions (e.g., a letdown sequence followed by an expression sequence), or operate according to a user input, or both.

Another significant advantage realized by the present invention is the ability to precisely regulate pressure changes within the breastshield chamber, so as to control pressure during a pumping cycle through a plurality of desired set points, including in some cases to less than ambient (atmosphere) during part of a cycle and then back to a maximum negative pressure.

An object of the present invention is to control minimum and maximum vacuum levels at the breastshield to alleviate issues associated with system volume, i.e., the volume of air in the system. Another and related object of the present invention is to enhance development of advanced systems, i.e., miniaturization of a breastpump system, its physical size, and power requirements, by decreasing the amount of work per suction cycle and therefore energy expended; the less work, the longer the battery life for a battery operated pump. Also, a potentially smaller motor can be used at reduced motor speed (for less noise).

Maintaining a minimum (or partial) vacuum also serves to minimize elastic rebound of the nipple seen in conventional systems that return back to atmospheric pressure. As the breast or nipple pulls into or retracts back within the breastshield, the system volume changes. The present invention allows for a more stable volume upon which the pump must act. A more stable volume also alleviates discomfort and irritation by minimizing the reciprocations of the breast or nipple within the breastshield. Milk may also continue to be removed during the baseline vacuum.

Additionally, the duration vacuum is applied to the breast to actively remove milk can be precisely controlled. An intelligent system, or "smart pump", can replicate a desired curve (suction pattern, or sequence) during each cycle.

Another object of the present invention is to maintain a minimum vacuum to hold or assist the hold of the breastshield onto the breast by suction for a "hands free" use, or partially hands free feature in some instances.

Another object of the present invention includes a valve that opens in a milk catch chamber due to differential pressure across the valve, where that pressure differential assists in opening the valve. The valve opens to allow the milk accumulated above the valve to empty into the collection container. In one form of the present invention, milk is actually drawn (forced) through the valve and into the container by a vacuum present in the container. This allows the use of more robust valves to pass milk through the valve using the vacuum in the collection container. The differential pressure allows for the utilization of check valves, e.g., a "duckbill" valve, with higher opening forces as well as a wider range of opening forces to maintain reliable operation and longer life.

In yet another aspect of the invention, a regulated pressure within a breastshield chamber of a breastpump allows for consistency between: pump cycle to pump cycle; mother to mother; and pump session to pump session, such as may be due to variable (breast to breast), or changing (nipple moving into and out of the breastshield during the pumping cycle) system volume within the breastshield.

With a pressure sensor, a very precise pressure curve can not only be achieved, but tailored as desired, and then reproduced at a later pumping session.

In yet another embodiment, the breast pump includes a pressure control system having a valving arrangement that is located at the vacuum pump, rather than at or on the breastshield assembly. In one form of this embodiment, three one way valves are used. Two are an umbrella and duckbill combination; the third is a flap or reed valve that is used to purge excess air from the system. All valves are statically closed and are opened by pressure across the valve, i.e., they are operated pneumatically.

Outside of the breastpump environment, embodiments of the present invention have potential application to what is referred to as negative pressure wound therapy. The latter is generally described in the BlueSky Medical Group, Inc. Chariker-Jeter or Wooding-Scott drainage kits, and Chariker, M. et al., Effective Management of Incisional and Cutaneous Fistulae with Closed Suction Wound Drainage," *Contemporary Surgery*, vol. 34, pp. 59-63 (June 1989). A reduced pressure, which may be intermittently applied, has been shown to have therapeutic benefit upon wound treatment and healing.

These and other features and advantages of the present invention will be further understood and appreciated when considered in relation to the following detailed description of embodiments of the invention, taken in conjunction with the drawings, in which:

BRIEF DESCRIPTION OF THE DRAWINGS

FIG. 23 is a sectional view of a breastshield similar to that of FIG. 2, for another embodiment of the present invention having a modified valve mechanism like that of FIG. 13;

FIG. 24 is a base mounting member for use with the embodiment of FIG. 23;

FIG. 25 is an enlarged elevational sectional view of the base mounting member of FIG. 24;

FIG. 26 is a top perspective view of a valve membrane for mounting on the base mounting member of FIG. 24; and FIG. 27 is a bottom perspective view of the valve membrane of FIG. 26.

DETAILED DESCRIPTION OF EMBODIMENTS OF THE INVENTION

Figure 1:
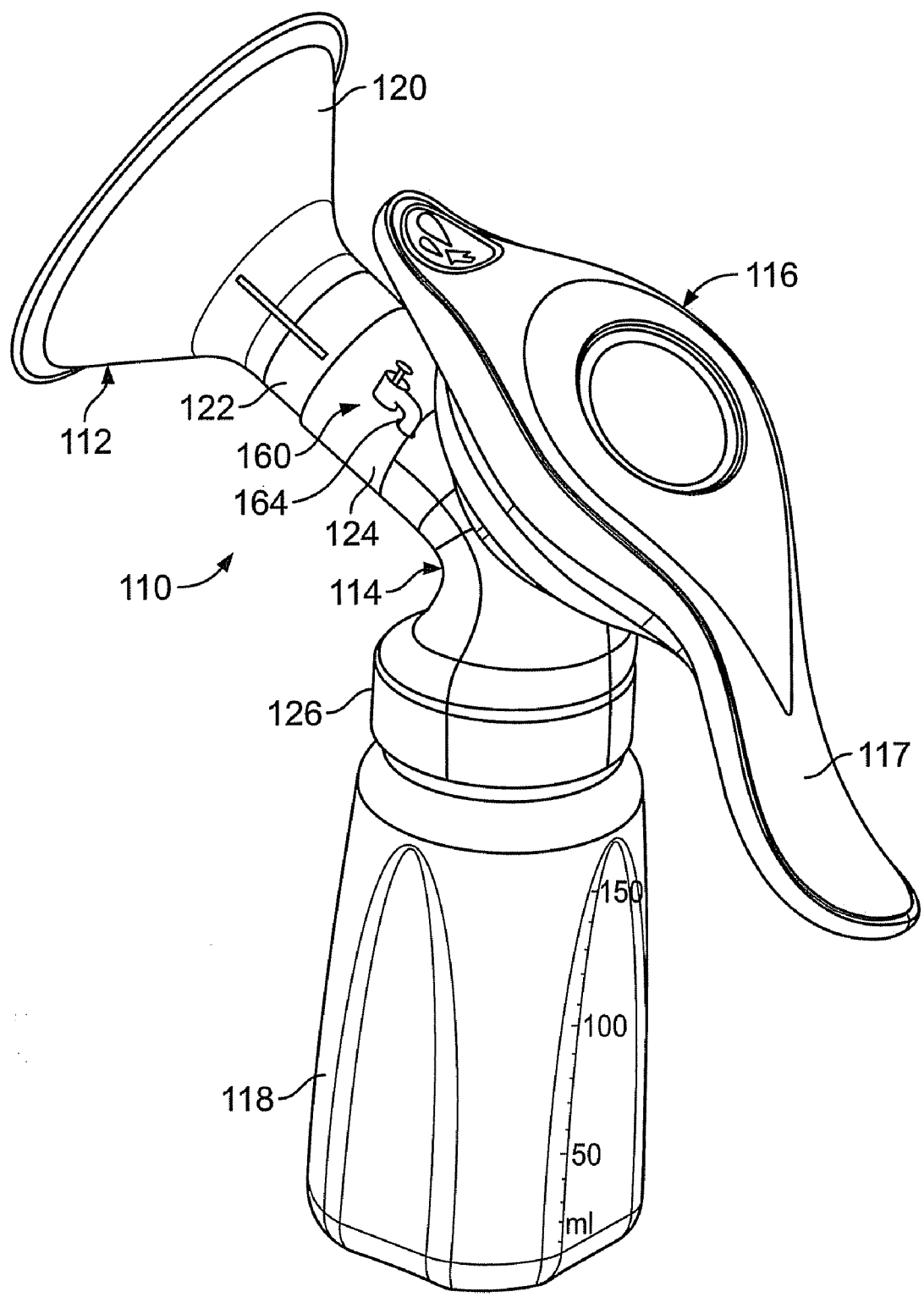
FIG. 1 is a perspective view of an embodiment of a manual breastpump according to certain aspects of the present invention.
Figure 2:
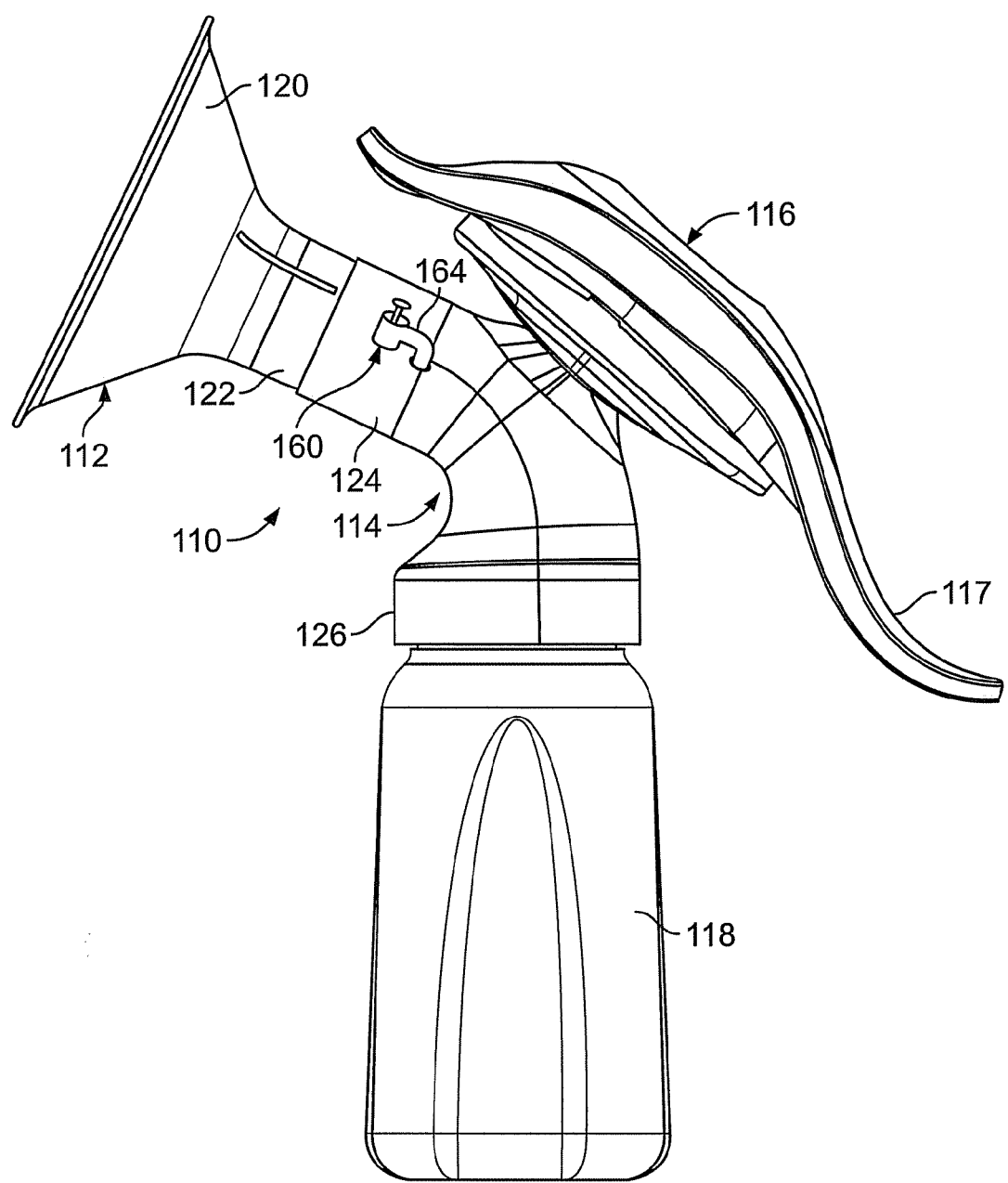
FIG. 2 is a side view of the breastpump of FIG. 1.
Figure 3:
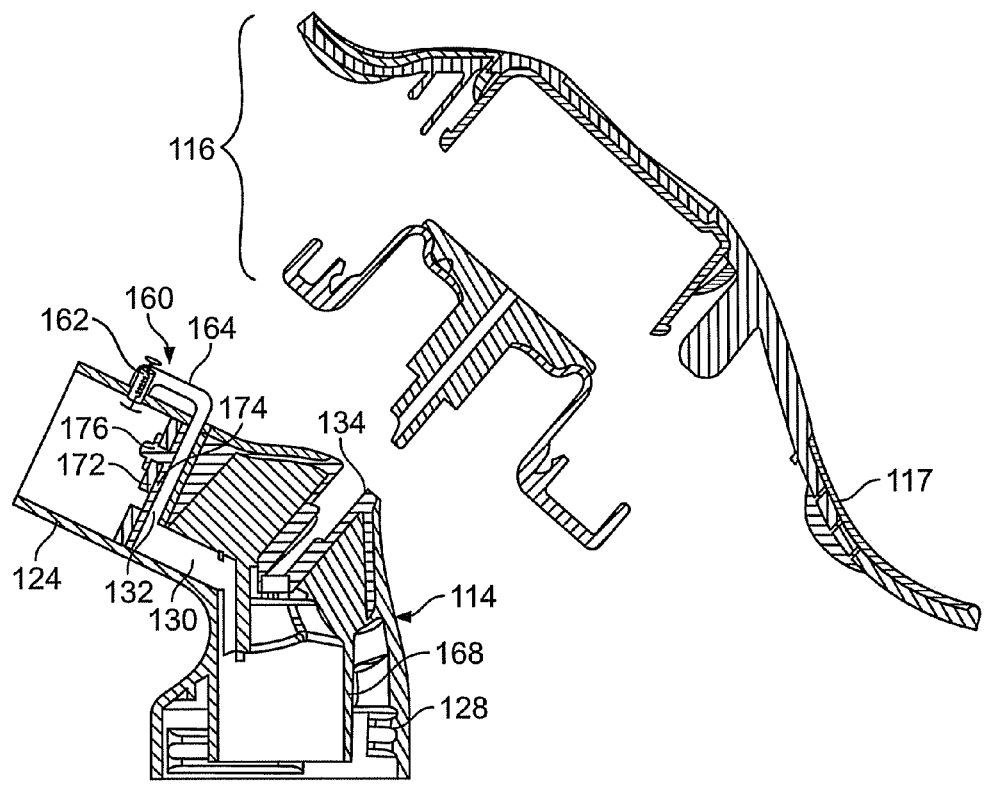
FIG. 3 is an exploded sectional view of the majority of the breastpump assembly of FIG. 1.

One embodiment of the invention is shown in a manual breastpump of FIGS. 1 through 3, here of the type as detailed in U.S. Publication No. 2004/0039330, incorporated herein by reference. This type of breastpump is simply illustrative, and not intended to be limiting of the invention.

The breastpump assembly 110 includes a shield 112, for contacting the breast. The shield 112 is attached to a conduit structure 114. A vacuum pump mechanism 116, in this instance a handle (lever) 117 which is hand-driven, is attached to the conduit structure 114. The conduit structure 114 transmits vacuum generated in the vacuum pump mechanism 116 to the shield 112, and transmits expressed breastmilk from the shield 112 to an attached container 118.

The shield 112 has a generally funnel portion 120 shaped and sized for being received onto a breast. The shield 112 extends into a sleeve 122 downstream from the funnel shaped portion 120. The sleeve, or nipple tunnel, 122 conducts expressed milk into the conduit structure 114. For purposes of the instant invention, the shape of the shield 112 and its formation with the conduit structure 114 are generally incidental to the invention; again, the particular arrangement and details of these elements is in no way limiting.

The conduit structure 114 is attachable to the shield 112 through a shield mount 124 sized and shaped to receive the sleeve 122. The conduit structure 114 is generally a housing (base) that interconnects and permits fluid communication between parts of the breastpump assembly 110 that includes not only milk flow, but also pressure (e.g., vacuum) communication. Here, the conduit structure 114 connects to the sleeve 122, by way of the shield mount 124 at an upstream end, and terminates with a valve mechanism (not shown in FIG. 3) as is known in the art (see the aforementioned patent publication disclosure) at a container attachment end 126. The container attachment end 126 may include threads 128 (FIG. 3) or any suitable mechanism for releasable attachment to container 118, which may be in the form of a milk bottle or the like. In FIG. 3, the conduit structure 114 includes a channel 130 for conducting expressed breast milk from the shield mount 124 and into the container 118. The conduit structure 114 also includes a receptacle or well 134 for receiving the pump mechanism 116 and conducting the air pressure change (here, a vacuum) effected by movement of the pump handle 117, with its related expansible chamber device (again, see the aforementioned patent publication disclosure).

A pressure regulator 160 (shown highly schematically, but of a type well known in the art) has the ability to regulate the pressure within the breastshield 112 so as to control pressure during a pumping cycle. A very easy manually operated regulator 160 is provided that operates so as to set a specific vacuum level to maintain a minimum level within the breastshield during expression of breast milk. The regulator 160 in this instance is manually operated, and of the general type disclosed in U.S. Pat. No. 4,964,851. Besides manually adjustable regulation, regulation can be automated, as discussed more fully below with respect to alternate embodiments, or the regulator mechanism can further made unadjustable in certain embodiments, also as discussed below.

Figure 4:
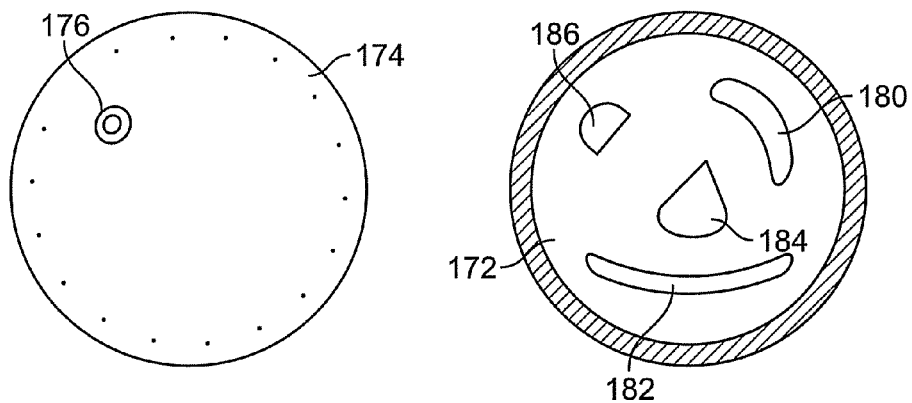
FIG. 4 is an enlarged view of the parts of one valve mechanism of the breastpump of FIG. 1.

As shown in FIG. 3, the regulator 160 works in conjunction with a valve mechanism to allow for the milk drawn from the breast to travel to the collection container 118, while maintaining a minimum vacuum in the breastshield. More particularly in reference to FIGS. 4 and 5, the valve mechanism generally consists of a rigid wall or base 172 and a thin flexible membrane 174 (or flap), made of rubber or silicone rubber; such is detailed in U.S. Pat. No. 4,929,229, incorporated herein by reference. The wall 172 is circular (disk-like) in shape, and can either be removably engaged or integrated with the shield mount 124. Wall 172 includes four openings 180, 182, 184, 186. Opening 184 is located at a point that is roughly at the center of the wall 172. Openings 180 and 182 are formed through the wall 172 along the bottom of the wall 172.

Opening 186 is for engagement with the membrane 174. The thin flexible membrane 174 has a generally circular (disk-like) shape and is attached to the wall 172 by way of knob (nub) 176, which is engaged in opening 186 in a snap fit. The diameter of the membrane 174 is sufficient enough to completely cover the wall 172 and openings 180, 182, 184.

The valve mechanism 172, 174 is positioned within the shield mount 124 upstream of the channel 130.

Figure 5:
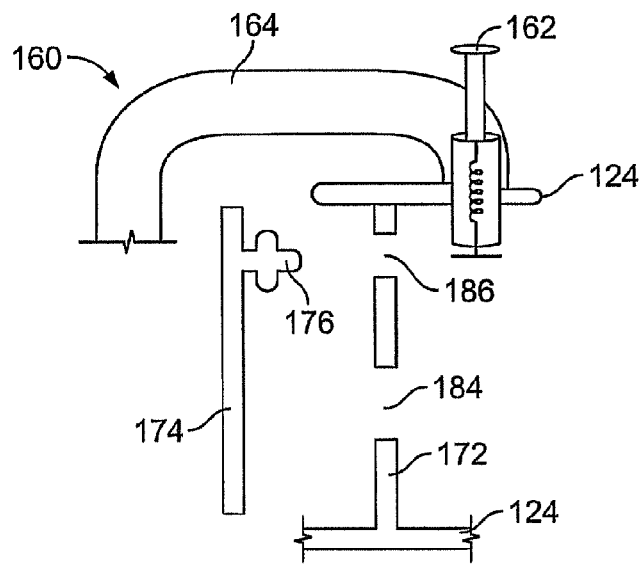
FIG. 5 is an exploded side sectional view of the valve mechanism of FIG. 3 and regulator.

Referring to FIG. 3 and FIG. 5, the regulator 160 includes a manual adjustment mechanism 162 located in a pressure channel structure 164. The regulator 160 is positioned within the shield mount 124 such that the adjustment mechanism 162 is accessible to be manually adjusted from the outside of the breastpump system. The pressure channel structure 164 extends outside the shield mount 124 to communicate at a second end with the channel 130. That is, the second end of the pressure channel 164 communicates with a gap 132 leading to the channel 130. Of course, the channel 164 could be made internal with the sidewall structure of the shield mount, or otherwise establish an air channel between the upstream and downstream sides of the valve 172, 174.

The pressure regulator 160 provides simple manual control for achieving and varying the negative pressure. The nursing mother can now maintain a desired minimum negative vacuum level, as follows.

The regulator 160 is adjusted to the level desired. As the cycle goes to (or at least toward) ambient pressure, the valve flap 174 engages the wall 172, closing off the breastshield from the rest of the breastpump. The negative pressure within the breastshield 112 continues to drop, however, as the system cycles back toward ambient from maximum negative pressure and higher pressure air passes through the pressure channel 164.

Vacuum in the breastshield 112 is maintained at the adjusted minimum while the nursing mother moves the pump handle 117 through the stroke until atmospheric pressure or even a slight positive pressure exists in the channel 130. A valve (not shown, but standard) between bottle 118 and milk retention chamber 168 that communicates with channel 130 opens to express the milk into the bottle.

With reference to FIG. 5, when the negative pressure reaches the preset minimum, regulator 160 closes, or shuts off air flow, maintaining the desired negative pressure within the shield 112. When the downstream vacuum level thereafter exceeds the preset minimum (e.g., desired, selected, or otherwise defined) on the next cycle, the valve 172, 174 opens.

It may be noted that the minimum vacuum maintained in the breastshield could be released through a relief element, for example, a relief valve positioned on the breastshield itself. The mother can also simply manipulate a portion of the breast to break the vacuum, or just pull the breastshield off her breast.

Figure 13:
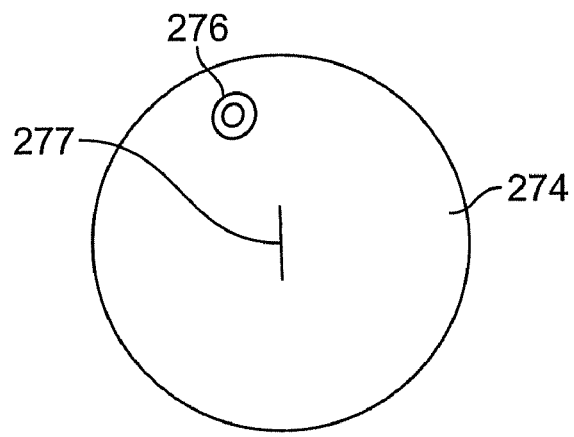
FIG. 13 is an enlarged view of the parts of an alternate embodiment of a valve mechanism of the type that could be adapted for the breastpump of FIG. 1.

An alternate embodiment of the thin flexible membrane 274 is shown in FIG. 13. This embodiment includes a slit 277 along with nub 276 for a snap fit engagement (the latter on the base 172). The slit 277 is located substantially in the center of the membrane 274, but any position of the slit is contemplated such that it opens and closes at a desired pressure. In this FIG. 13 embodiment, the slit is sized in conjunction with the natural resilience (elasticity) of the membrane, so that it closes at the desired minimum vacuum (say, negative 50 mmHg). There is no ability for the user to adjust the minimum vacuum (since there is no adjustable regulator used in this version), but a very simple mechanism for maintaining a desired pressure is provided. It is nonetheless tailorable (via slit manufacture) at the factory, for example, to an approximate desired minimum vacuum, and is reasonably durable. There are other ways to do this slit-like concept, such as one or more pinholes, for example, which would remain open until the pressure reached the point where the natural resilience of the material defining the hole(s) causes closure.

Yet another alternative for the thin flexible membrane 274 is shown in the embodiment of FIGS. 23 through 27. As shown in FIG. 27, this flexible membrane 850 has two slits 277, which are shown generally parallel and slightly spaced apart. These slits 277 are formed through an enlarged nub 852. Nub 852 has a planar part 854 (within which the slits 277 are formed), and a somewhat radially widened circumferential bulge or annulus 856 between the planar part 854 and the major planar ringlike part 858 of the membrane. Reinforcing bumps 860 are formed on the downstream end of the ringlike part 858 (downstream relative to milk flow, as will hereafter be evident in discussion of the mounting of the membrane 850). These reinforcing bumps 860 serve to stiffen the membrane against being drawn into apertures (or otherwise deformed) in the base or mounting member to which it is attached, and with which it functions to form a valve.

That mounting member 862 is shown in FIGS. 24 and 25. Mounting member 862 is a short cylindrical piece having a sidewall 864 and a planar ringlike base 866. The ringlike base 866 extends radially outwardly on one side surface into a shoulder 868, which circumscribes this side of the mounting member. Holes 870 are formed through the base 866 around its surface, through which fluid (milk or air) may flow; while circular holes are shown, other shapes (e.g., kidney) could be used for the throughholes. A nub-receiving aperture 872 is formed generally centered on the base 866. The nub 852 is received in this aperture 872, with the bulge 856 passing therethrough from one side to the other, with the now downstream side of the bulge 856 then serving to fix the membrane in place by engaging with the upstream side of the mounting member 862. The ringlike part 858 of the membrane is sized to cover the holes 870, and generally extend to about the shoulder 868.

The mounting member is adapted to fit over the downstream end of the nipple tunnel 878 of the breast shield 876, which has a funnel part 880. To that end, the mounting member 862 has an angulated upstream end to fit over the outside of the nipple tunnel in an interference fit (or it could be made to flex inwardly to mount within the nipple tunnel in a similar manner).

This double-slit 277 version is considered to give better minimum vacuum control over a broad range of maximum vacuum.

Figure 14:
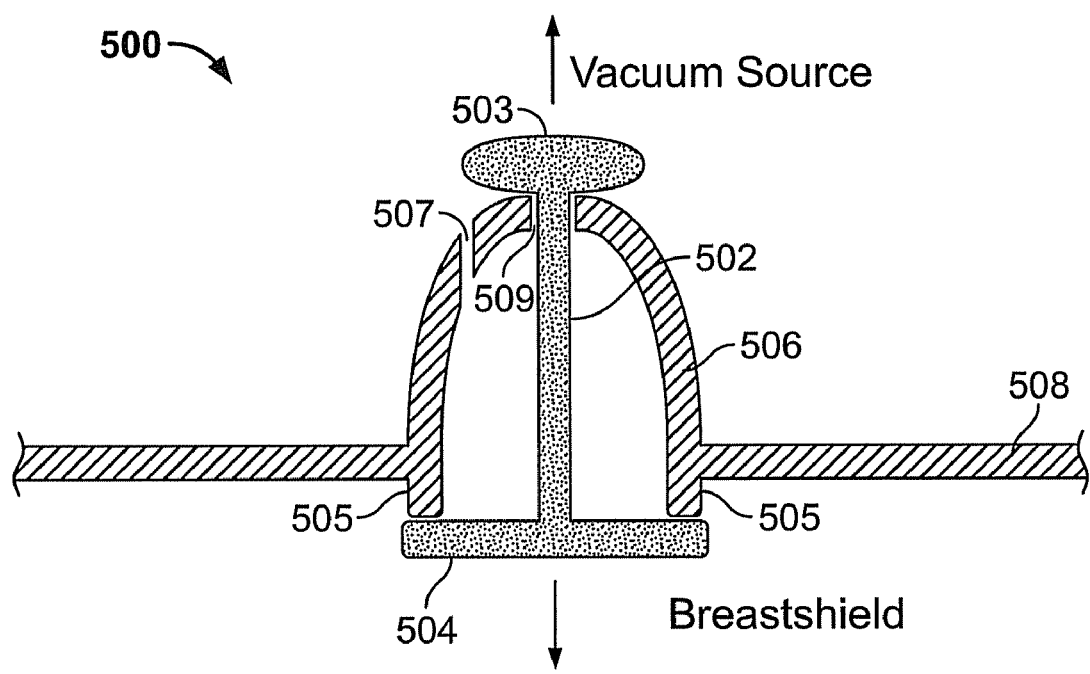
FIG. 14 is a side view of an alternate embodiment of another regulator.

Another embodiment of a simple but robust pressure regulator is shown in FIG. 14. As shown in FIG. 14, the regulator 500 includes a rigid pin 502 having disks 503 and 504 at each end thereof. The regulator 500 can move along the longitudinal axis of the pin 502 within a dome 506. Dome 506 is fixed in, or as shown here made integral with, a flexible membrane 508, such as that described vis. flap 174. Dome 506 is thus flexible, and essentially forms a spring-like element. That is, dome 506 is sized with the pin 502 so that the dome 506 presses the disk 503 away from the membrane 508 while simultaneously pulling the disk 504 in sealing engagement with a seal ring 505. The amount of force exerted by the dome 506 on the pin 502 is tailored to the minimum vacuum desired. An opening 507 is formed through the dome to allow air to pass from one side of the membrane to the other. Alternatively, the hole 509 through which the pin passes can be adapted to yield this air pass in operation. As noted, the regulator 500 is adjusted to shut at the minimum vacuum; when the negative pressure within the rest of the breastpump drops toward ambient, the flap 508 closes against the base as previously discussed. The vacuum within the breastshield then causes the disk 504 to unseat, allowing the higher pressure air to be pulled into the breastshield through the hole 507. The minimum pressure is reached within the breastshield when the pressure differential is no longer enough to overcome the spring force exerted on the disk 503 by the resilient dome 506, and disk 504 seats. Yet other forms of a simple yet robust regulator that could be adapted for use with the invention would be an umbrella valve, a duckbill valve or a combined umbrella/duckbill check-relief valve, such as that described in U.S. Pat. No. 3,159,176.

Figure 16:
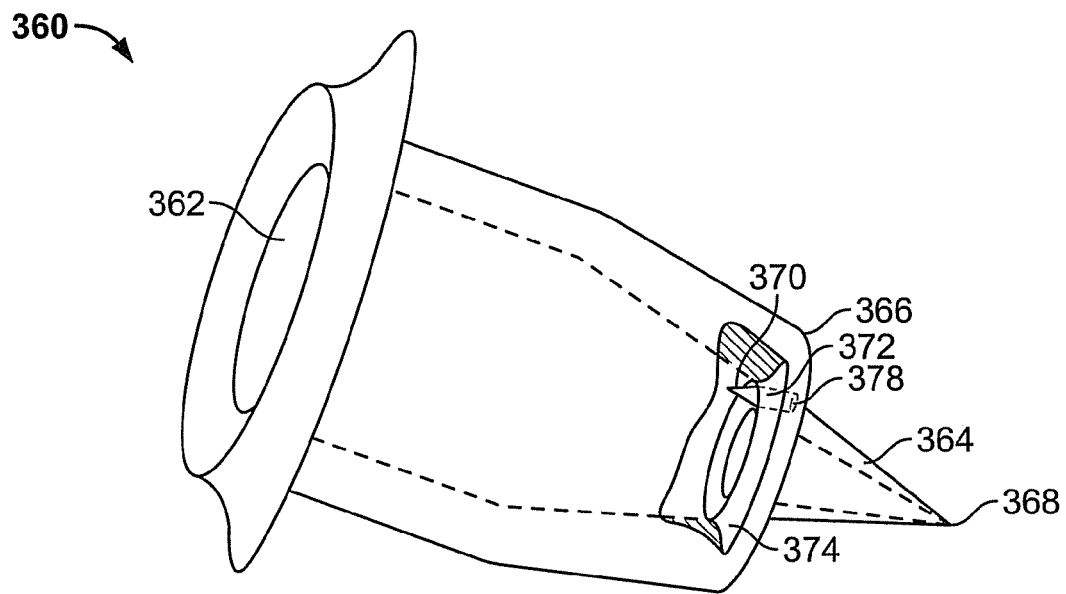
FIG. 16 is a perspective view of another embodiment of the invention using two duckbill valves.
Figure 17:
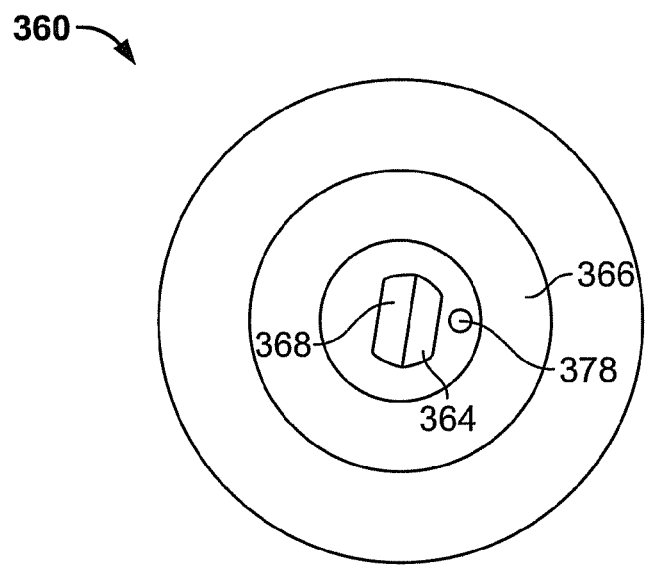
FIG. 17 is a downstream end view of the embodiment of FIG. 16.

FIGS. 16 and 17 show yet another variant which uses two duckbill valves to establish and maintain the minimum desired vacuum. This type of breastshield is a monolithic version made of a flexible silicone, such as disclosed in U.S. Patent Publication 2005/0222536, filed Mar. 31, 2005. The nature of the breastshield is of course merely incidental to the invention, as previously noted. Breastshield 360 has an opening 362 to receive the nipple and some surrounding breast. Downstream from the opening 362 is a first duckbill valve 364 which seals this downstream end 366 of the breastshield. The first duckbill valve 364 is of a conventional construction, also being made of a flexible material, with a downstream opening for this valve at 368.

A second duckbill valve 370 is located in a conduit or throughbore 372 formed through the upstream flange 374 of the first duckbill valve 364. It is generally the same type as the first duckbill valve 364, but much smaller. The downstream end of the throughbore 372 terminates in an opening 378 which communicates with the vacuum being generated for the breastshield in general. The upstream end of the throughbore 372 communicates with the interior of smaller duckbill valve 370. Smaller duckbill valve 370 is designed to close at the minimum pressure (vacuum) desired to be maintained inside the breastshield throughout a pumping cycle.

This is how the foregoing double-duckbill embodiment works. When the pumping sequence goes toward ambient within the system, first duckbill valve 364 closes (higher pressure now being present downstream than within the breast shield interior). The pressure differential nonetheless causes air to pass through smaller duckbill 370, however, to the interior of the breastshield, until the natural (and preselected) resilience of the smaller duckbill valve 370 causes it to close, at the minimum desired vacuum to be maintained.

Of course, the invention is readily adaptable for a motorized breastpump. The breastpump may be manually adjustable to produce simple vacuum and cycle frequency conditions within the breastshield, or may be user programmable as detailed in U.S. Pat. No. 6,547,756 for more complex pumping cycles or curves, or may have both capabilities.

As previously noted, the invention has application beyond a breastpump environment. For example, the embodiment of FIGS. 16 and 17 could be adapted for negative wound therapy. The opening 362 would be widened, for instance, and the axially extending portion 380 made much shorter. The rest of the system would need little or no modification to adapt to this other therapeutic application.

Figure 6:
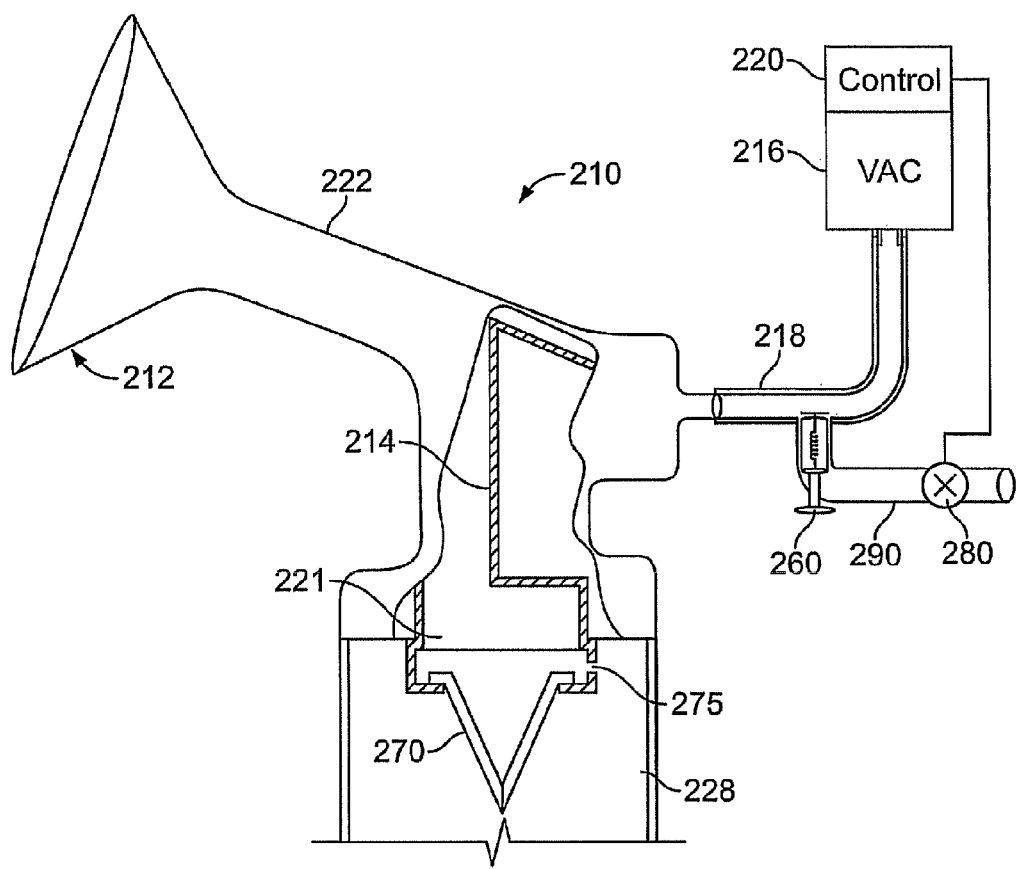
FIG. 6 is a side elevational view, partly broken-away and also schematic, of another embodiment in a motor driven breastpump according to certain aspects of the present invention.

As shown in FIG. 6, this breastpump assembly 210 includes a shield 212, shaped and sized for being received onto a breast. The shield 212 is attached to a conduit structure 214. A vacuum pump mechanism 216 is attached to the assembly 210 via an airline 218. The pump 216 is controlled by a controller 220. The airline 218 transmits vacuum generated in the vacuum pump 216 to the shield 212. The airline 218 includes an adjustable pressure regulator 260 that regulates the vacuum level within the breastshield 212 when valve 280 is open.

The conduit structure 214 conducts expressed breast milk from the breastshield 212 through a duckbill valve mechanism 270 and into the milk container 228. A vent 275, as further described below, is used in conjunction with the valve 270.

A solenoid valve 280, which is operated by the controller 220, is in series with the regulator 260, in ambient airline 290.

The manually adjustable regulator 260 has the ability to regulate the minimum negative pressure within the breastshield 212 (in the manner previously described with reference to regulator 160). In this instance, it is located in the vacuum line 218 and the line to ambient pressure 290.

As noted, solenoid valve 280 is operated by the controller 220, which controls the pumping cycle. Controller 220 can be of many types, from a simple mechanical device that functions to operate the solenoid valve at a preset time or pressure in a cycle, to a microprocessor programmed to do the same. With the solenoid valve 280 closed (and the pump running), the vacuum increases in the breastshield 212 to a desired maximum whereupon the solenoid valve 280 is opened, so the vacuum decreases in the breastshield 212 toward ambient. When the negative pressure within the line 218 reaches the preset minimum of regulator 260, the regulator closes, and line 290 is closed off from line 218. This maintains a minimum negative (vacuum) level in the breastshield 212. The solenoid valve is then closed to start the next cycle.

In use of the motorized breastpump, the assembly 210 system is initially at atmospheric pressure (or about 0 mmHg negative), the solenoid valve 280 and duckbill valve 270 are closed upon the initiation of vacuum build-up. The regulator 260 is set to a predetermined value (e.g., 50 mmHg negative). The vacuum in the breastshield 212 increases to a maximum value, as for example a value used for milk expression, usually around 250 mmHg vacuum. Once the maximum value is achieved, the pump 216 stops drawing a vacuum and the solenoid valve 280 opens such that the assembly 210 returns toward atmospheric, which causes the vacuum in the breastshield 212 to decrease. When the preset minimum vacuum is reached, however, the regulator 260 shuts the line 290, holding the system at the minimum vacuum.

Expressed milk is collected within the catch chamber 221 above valve 270. It will be noted that vacuum is also being generated in the container 228. This is where the vent 275 comes into play in a unique manner. The vacuum in the container 228 increases as the air flows from the container 228 into the breastshield conduit structure 214 via the vent 275. This somewhat incremental increase in negative pressure within the bottle 228 ultimately is used to cause the valve 270 to open and drop milk into the container 228. Subsequent cycles thereafter experience this differential pressure across the valve 270 such that milk then drops through valve 270 into the container 228 during each cycle thereafter due to the vacuum in the container 228 being greater than the vacuum in the breastshield 212.

Figure 11:
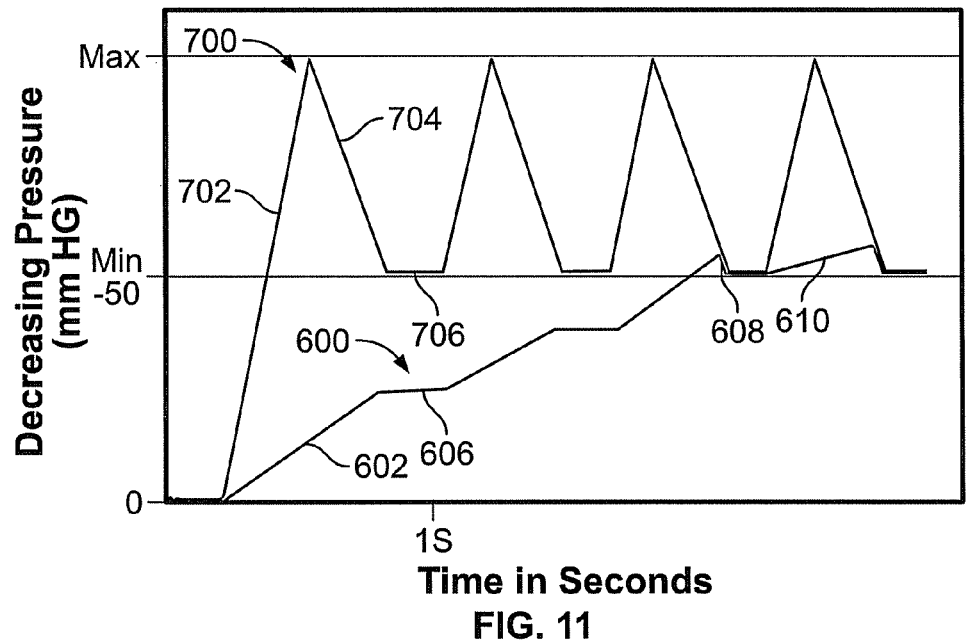

More particularly, FIG. 11 represents such a method for operating a breastpump between differing maximum and minimum vacuum levels by regulating and tailoring pressures within the breastshield conduit structure and the corresponding pressure within a collection container. The amount of pressure illustrated is shown at 0 mmHg negative (i.e., ambient), with cycles maintained between a minimum pressure of about −50 mmHg and maximum pressure of about −240 mmHg. Curve 700 represents the pressure within a breastshield while curve 600 represents the corresponding pressure within a bottle. In reference to an automated pump such as that of FIG. 6, the system is at atmosphere when the breastpump begins operation. The solenoid valve 280 and duckbill valve 270 (upon initiation of vacuum) are closed. The regulator 260 is set to a minimum pressure, −50 mmHg in this example. As the vacuum in the breastshield 212 increases, represented by segment 702 in FIG. 11, the vacuum in the bottle 228 increases toward the minimum pressure (segment 602). Although not shown on FIG. 11, it may take several cycles before the vacuum in the breastshield reaches the maximum level because of the initial removal of air from the bottle. Once a maximum vacuum is reached, e.g., −240 mmHg, the solenoid valve 280 opens, and the breastshield (and communicating internal structure) then returns back to the minimum pressure. As the system returns back to the minimum pressure (which is still less than atmospheric pressure), the vacuum in the breastshield 212 decreases (graph segment 704) while the vacuum in the bottle 228 continues to increase. At the end of the pumping cycle, the minimum pressure is reached in the breastshield 212 causing the regulator 260 to close the line 290. The vacuum in the breastshield 212 maintains the minimum pressure for a duration of time (graph segment 706), while the vacuum in the bottle 228 increases (becomes more negative) slowly due to flow through vent 275. The above described pumping cycle repeats a number of times, eventually creating a negative pressure in the bottle 228 (graph segment 608, and more particularly 610) from additive vacuum, that forces the duckbill valve 270 open, so milk from the breastshield 212 flows into the collection container 228. What this therefore enables is the use of far more robust valves between the conduit structure and milk container. The pressure differential created between the bottle and milk catch chamber 221 is utilized to essentially propel the milk through the valve.

Figure 19:
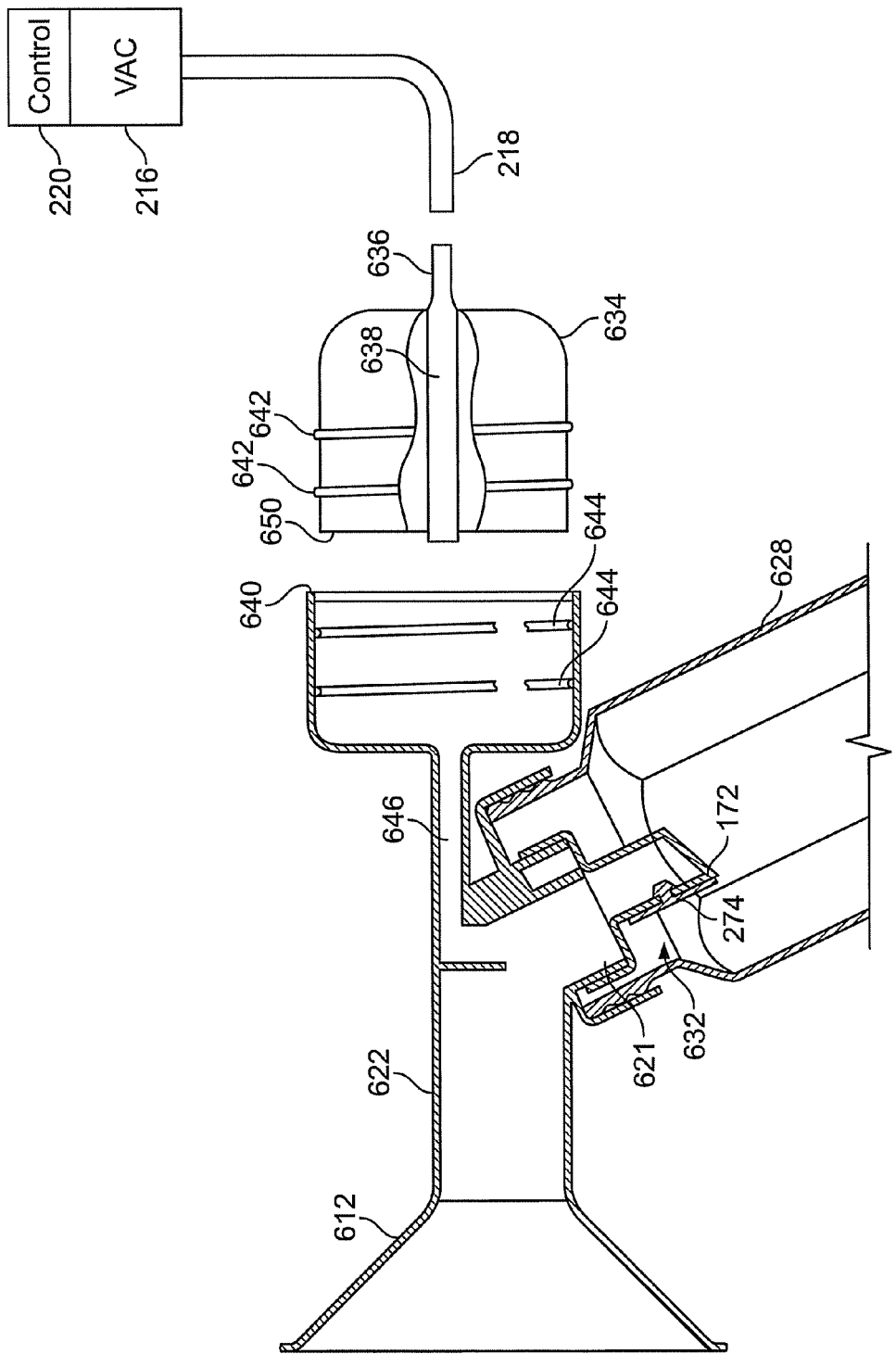
FIG. 19 is yet another variation on the inventive theme. This version is adapted to function with a vacuum source 216 which draws the vacuum to the desired minimum, but without necessarily venting portions of the system to ambient (as done in some of the other embodiments).

More particularly, FIG. 19 has a conventional shield 612 and nipple tunnel 622. A catch chamber 621 is downstream therefrom, and has a valving mechanism 632 very much like that described in U.S. Pat. No. 4,929,229 (general details of which can be gleaned from that patent). The membrane used herewith, however, is membrane 274 described above (and illustrated in FIG. 13 herein) as used in conjunction with the base 172 (described, for instance, with respect to FIG. 4).

This FIG. 19 embodiment can be used with both a manual pump or a motorized pump 216. Here, it is depicted for use with a motorized pump. An adapter 634 is shown, which has a nipple 636 that connects with an airline 218 from the vacuum source 216. That nipple 636 extends to an internal tube 638, which fits within a conduit 646 as hereinafter described.

Adapter 634 mates with a collar part 640 of the breastpump via external threads 642 on adapter 634 that are match-threaded with internal threads 644 to the collar 640. Collar 640 has an opening extending into conduit 646, which communicates with the breastshield 612.

It will be noted that this, as well as other embodiments of the invention, may further employ various means to separate the vacuum source from the breastshield, for hygienic reasons as well as to protect the vacuum source from moisture. Various such media separating techniques have been developed, as by Applicants' assignee Medela, and can be found in U.S. Pat. No. 6,676,631 (see, e.g., FIG. 20 thereof), U.S. Pat. No. 5,941,847 and U.S. Ser. No. 11/591,276 (filed Nov. 1, 2006), just to name a few.

Figure 7:
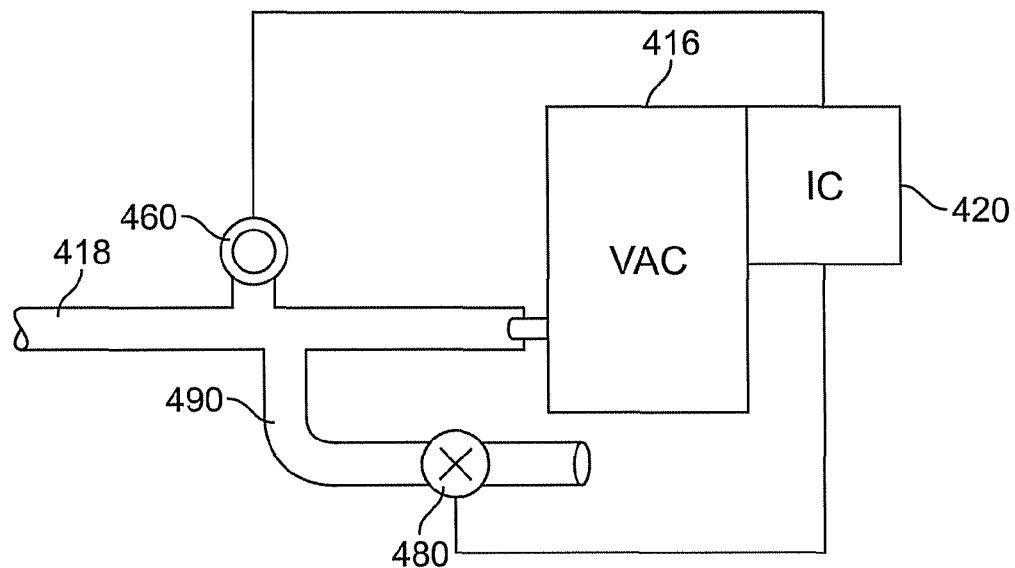
FIG. 7 is a schematic view of another arrangement for controlling pressure in a breastpump of the type of FIG. 6.

Returning now to FIG. 19, this embodiment uses a vacuum sequence that does not return to ambient, but instead takes the vacuum down from a maximum (e.g., about −250 mmHg), to the desired minimum (e.g., about −50 mmHg), until once more returning to the maximum. This is essentially a "closed" system. Milk that is expressed collects in the catch chamber 621 until the retained vacuum in the bottle 628 exceeds the minimum vacuum in the rest of the system. Using the membrane with slit (274, 277), vacuum developed in the bottle at the maximum end of the cycle does not completely return to the minimum (through selection of an appropriate cycle rate and slit 277 size). After a number of initial cycles, the vacuum building in the bottle permits the membrane 274 to unseat, and milk in the collection chamber to pass therethrough.

Where a manually operated regulator is shown in FIG. 6, an automated pressure regulated system is shown in FIG. 7. A vacuum pump mechanism 416 includes a vacuum line 418 and a solenoid valve 480 in an ambient airline 490. The pump 416 is controlled by a microprocessor based controller 420, which further controls the solenoid valve 480 and is connected with a pressure transducer 460.

Figure 8:
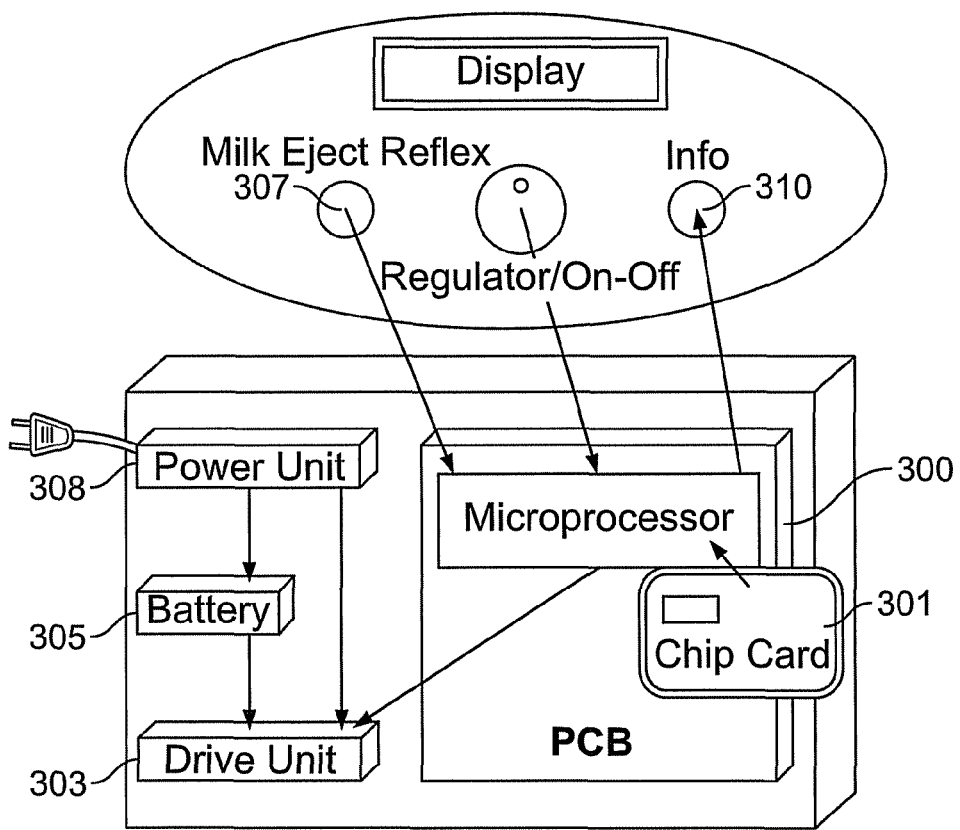
FIG. 8 is a diagrammatic representation of various components of a computer operated breastpump according to another embodiment of the present invention.

The range (maximum, minimum and anywhere in between) of pressure values can be pre-programmed, or programmed by the user. With reference to FIG. 8, for example, the breastpump utilizes a microprocessor-based system indicated at 300, which is provided user input through a plurality of "chip" cards 301. Each chip card contains one or more predetermined programs that either varies pressure levels or maintains a specified pressure level within a breastshield, recorded on an EEPROM. For example, each card could contain a specific type of vacuum curve, or combination of curves, to be realized within the breastshield. More detail of this kind of programmed sequence generation can be found in U.S. Pat. No. 6,547,756. As also described therein, many other input mechanisms can be used to set or adjust the pumping curve(s). Other input means could be used, such as more dedicated buttons like button 307 for a "letdown" sequence, and button 310 for a pre-set baseline vacuum in the breastshield, each set to actuate a given pressure level or range into the microprocessor 300, and in turn to the breastshield. A numeric pad could be provided to input a code for a particular program cycle, as well as desired vacuum level set points.

The particular program selected is then communicated to the microprocessor 300. Microprocessor 300 is integrated with the drive unit 303 to effect operation of the pump and to control the pressure in accordance with the selected program, drawing upon a common power source (308 or 305).

Various maximum, minimum and pressure points in between can thus be set by the user or preprogrammed. Returning to FIG. 7, the pressure transducer 460 then can relatively precisely determine the pressure being effected, sending a signal back to the controller 420 to govern operation. In this embodiment, the solenoid valve 480 is operated to adjust the vacuum between pressure points, by variably opening and closing the valve in a controlled sequence. To operate the breastpump so as to maintain a desired minimum pressure, such as 50 mmHg vacuum in a cycle, the valve would be opened at the set maximum negative pressure, opening the system to ambient (the rate at which it is opened likewise giving some control over the curve being generated). At the point that the pressure transducer 460 detects (or anticipates achieving) the desired minimum, the valve is closed, cutting off ambient air and holding vacuum in the breastshield. The microprocessor may thus be provided with the capability to automatically transition the pressure within the breastshield from a maximum pressure to a minimum pressure (or ambient), and optionally to a pressure(s) in between.

It will be noted that there are electromechanical valves known in the art that could also be substituted and adapted for use in place of valve 270, for instance.

Returning to FIG. 11, for example, this foregoing system could be used to initially adjust the minimum pressure of the initial cycles to actually match that of the pressure build-up in the bottle, so that milk is dumped from the outset, rather than after several cycles. Graph point 706 would thus be moved downward (as shown in FIG. 11) to that of graph point 606 (through use of an initially lesser pressure (i.e., vacuum) than the −50 mmHg depicted), with subsequent "minimums" being likewise adjusted to increase until the desired −50 mmHg is reached.

Figure 18:
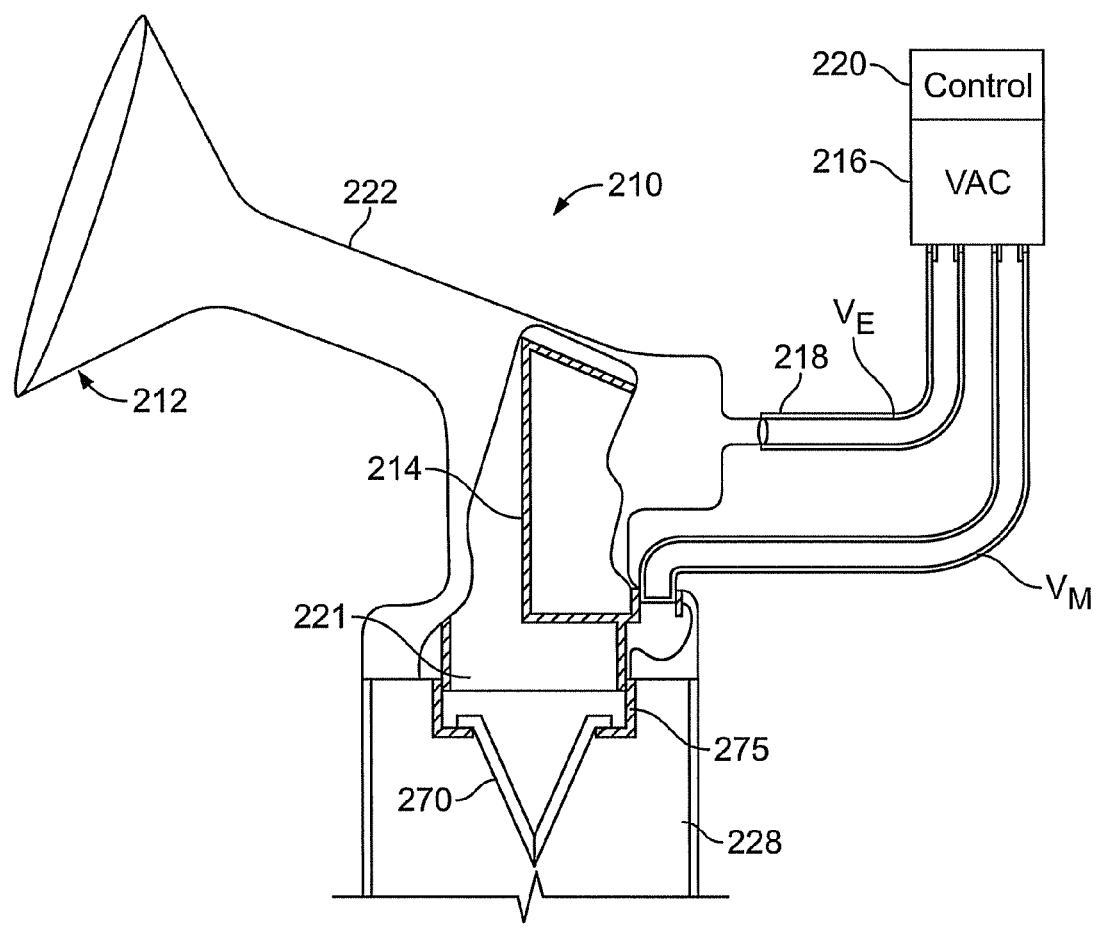
FIG. 18 is still another embodiment, similar in view to that of FIG. 6.

Looking at FIG. 18, yet another embodiment is seen. In this version, controller 220 is used to operate two separate vacuum lines $V_E$, $V_M$ from the vacuum source 216. $V_E$ is the source line for the milk expression cycle. $V_M$ is a line for conveying and maintaining a minimum baseline vacuum within the breastshield. Note that source 216 can also be different vacuum sources, which can be independent of each other and separately controlled.

It can thus be seen that a variety of different yet precisely determined actual pressures, as well as rates of change, can now be provided within a breastshield, all pressures being less than ambient for the majority of the pumping session, if desired. Examples of the kind of methods (curves) for operating a breastshield through a sequence having differing pressure less than ambient are further shown in FIGS. 9, 10 and 12.

Figure 9:
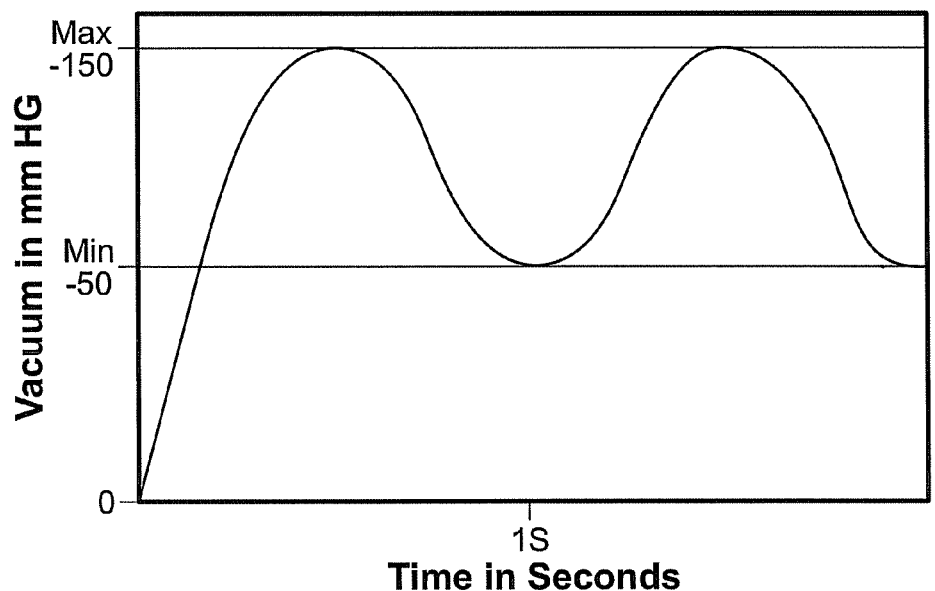
FIGS. 9 through 12 are various representative methods (curves) for operating a breastpump between differing maximum and minimum vacuum levels by regulating pressure.
Figure 10:
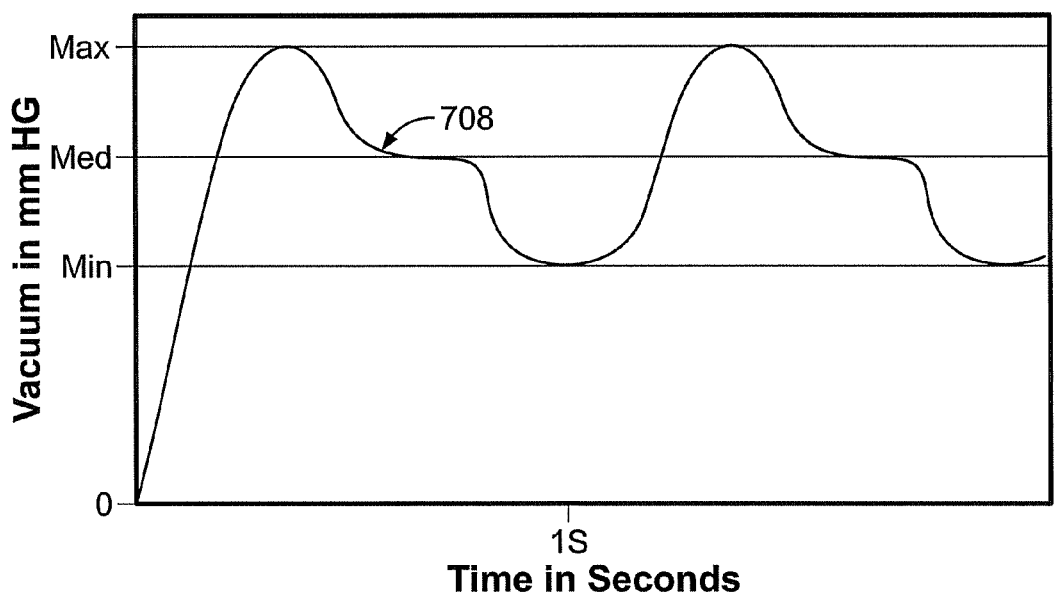
Figure 12:
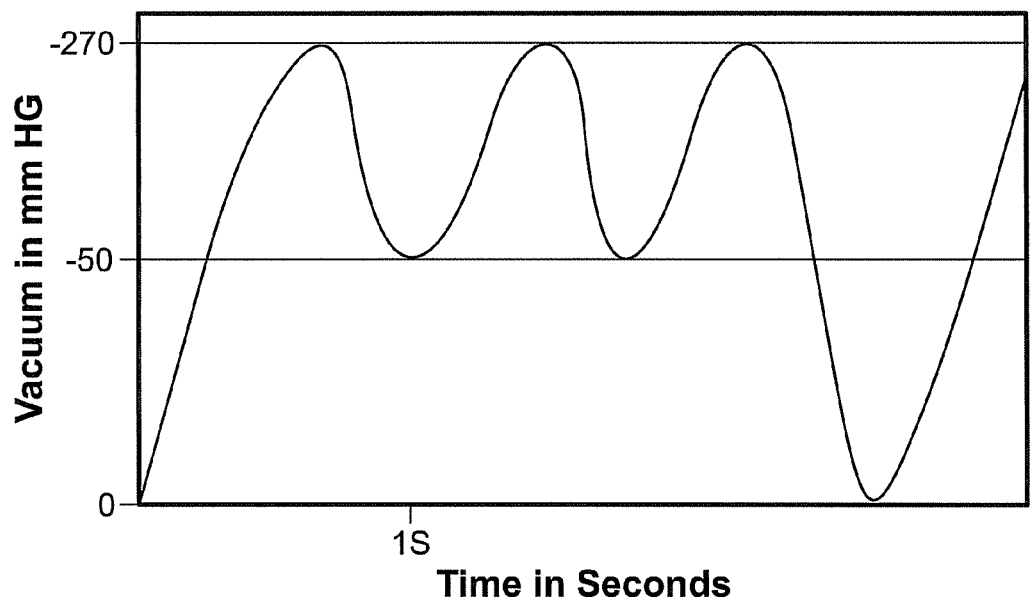

As indicated in the graphs of FIGS. 9, 10 and 12, negative pressure is along the y-axis (in millimeters of mercury) and time (in seconds) along the x-axis. The pressure is charted with respect to that expected to be realized in the breastshield of a breastpump assembly. In reference to the particular cycle or sequence of FIG. 9, the amount of pressure is less than 0 mmHg negative, more particularly, between a minimum and maximum pressure value, for example, −50 mmHg to −150 mmHg. The regulator maintains a vacuum within the breastshield between a minimum and maximum value along a relatively smoothly rising and falling sequence. While a "minimum" pressure of −50 mmHg has been generally discussed, present thinking of the Inventors yields a desired range between about 15 mmHg and about 60 mmHg negative pressure. For instance, it may be desired in one application of the invention to maintain the minimum vacuum at a level which will enable the breastshield (and related structure it is carrying) to be held in place through suction, in a "hands-free" mode of use. It will be noted that whether totally "hands-free" suspension of the breastshield is accomplished, the use of the minimum vacuum serves to keep the breastshield positioned about the nipple. Having the nipple become uncentered in a breastshield is undesirable, and the invention is very advantageous in that respect.

Figure 15:
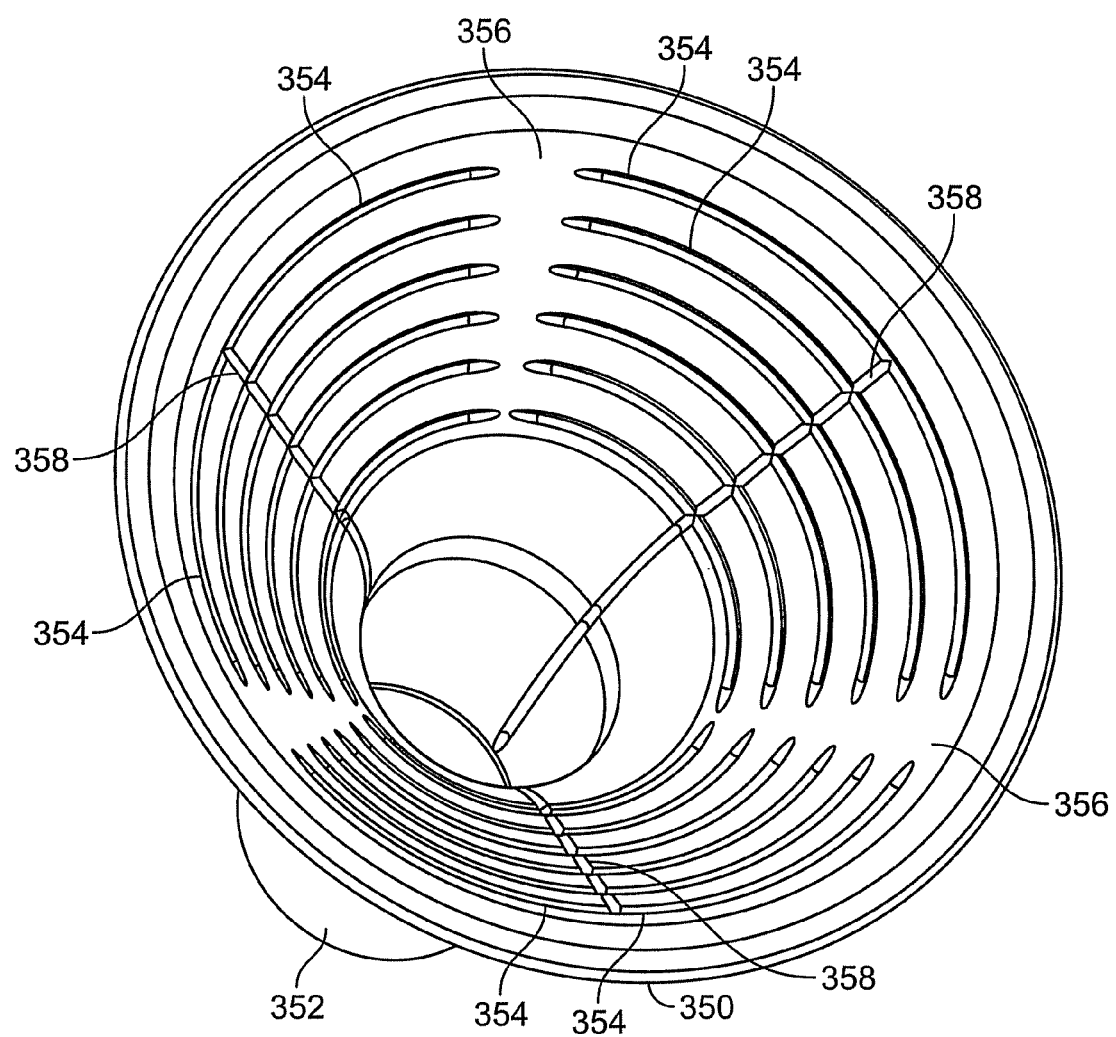
FIG. 15 is a perspective view of a "hands-free" type embodiment of a breastshield according to an aspect of the invention.

FIG. 15, for instance, shows an embodiment for a breastshield having a construction on the interior of the funnel surface considered conducive for "hands-free" use. Funnel 350 is of the type previously discussed with regard to shields 112, 212. On its interior surface, however, are a plurality of suction channels 354 formed concentrically about the axis of the funnel 350/nipple tunnel 352. The suction channels are periodically broken (as at areas 356). The suction channels 354 are open inwardly (i.e., facing the breast).

A series of vacuum channels 358 interconnect with the suction channels 354. These vacuum channels extend down into the nipple tunnel 352 to a point where they will extend past any breast and nipple tissue, so as to be open to the vacuum being generated in the breastshield at this downstream end. As can therefore be understood, the vacuum, such as a minimum vacuum, maintained in the breastshield will be conveyed by the vacuum channels 358 to the suction channels 354. A fairly broad area for suction between the funnel 350 and the breast therein is thereby established, which will serve to position, and if sufficient actually support in place, the breastshield. Of course many other designs can be readily conceived to convey and provide the foregoing "hands-free" type suction.

In another operation method, as shown in FIG. 10, the amount of negative pressure is given more complexity in the curve over time. More particularly, the regulator can be manipulated to control the pressure to a medium vacuum held for a period of time, between a minimum vacuum and maximum vacuum, for example, a medium vacuum of −175 mmHg (point 708) between −150 mmHg to −250 mmHg. FIG. 12 illustrates yet another possible variation when a maximum and minimum vacuum series of cycles is interspersed with a return to ambient. Plainly, the invention allows a wide variety of precisely controlled and tailored pumping sequences to be effected.

Figure 20:
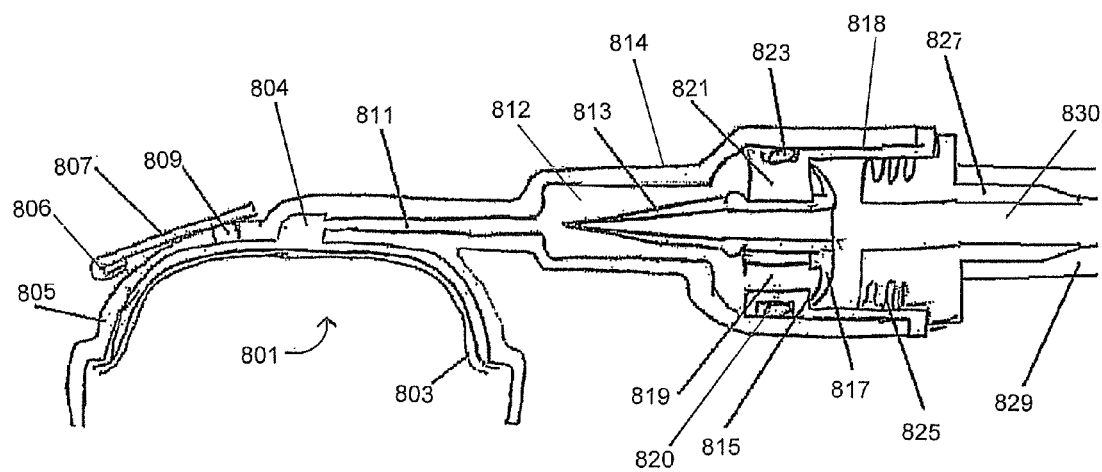
FIG. 20 is another embodiment of a pressure regulator.

Referring to FIG. 20, another embodiment of a pressure regulator used to maintain a minimum vacuum is shown. In this embodiment, the valving used is removed from the breastpump assembly itself, and place much nearer to the vacuum pump. The type of pump being used is a diaphragm pump, such as that used in the SYMPHONY breastpump sold by Medela, Inc. This embodiment also addresses, in part, two issues: air, from leakage into the breastshield through gaps between the interface of the breastshield and the breast, for instance, needs to be expelled from the system; so too, air that enters the region between the flexible membrane and the cap within which it reciprocates also needs to be expelled.

Referring once again to FIG. 20 now, the diaphragm pump is generally indicated at 801. It creates a vacuum by use of a membrane or barrier 803 which is reciprocated (in known fashion, but the mechanism of which is not shown) relative to a pump cap 805. As the membrane 803 pulls away from the cap 805, the expanded volume between the cap interior and the membrane generates a negative pressure, which is initially transmitted through the port 804 in the cap 805 and into conduit 811; here, this conduit structure is integral with the cap 805, although it need not be so. Cap 805 would itself snap-fit or interference fit on a base structure (also not shown) to which the membrane 803 is attached or fitted.

Downstream from the conduit 811 is a valving structure used to establish and maintain the minimum vacuum. Conduit or passage 811 opens into a chamber 812 formed by valving housing 814. The valving mechanism is an umbrella valve 817 that is combined with a duck bill valve 813; these could alternatively be separated along a common channel. Valving mechanism 813/817 seals against a surface bulkhead (or shoulder) 821, which has a passage 819 extending between upstream and downstream sides of umbrella valve 817. The umbrella valve 817 seals along its underside against surface 815. The duckbill valve 813 extends into the chamber 812.

The bulkhead 821 is itself part of a mounting assembly 818 which is designed to slide and fit within the housing 814, for easy insertion and removal of the valving mechanism. To this end, a packaging seal 823 (o ring) sits proud in a circumferential channel 820 of the bulkhead, to seal the two pieces when fit together.

The foregoing housing and mounting assembly connects to the breast shield assembly (not shown but downstream) by a hose 829. The hose 829 press fits onto a tube fitting barb 827 that is part of a plug having flanges yielding seal ridges 825. A channel 830 extends through the barb and plug.

Finishing this valving arrangement is a one way (antipressure) reed valve 807, which is mounted via a biasing hinge 806 to the cap in a manner to open and close (seal against) hole 809 that extends through the cap 805 into the space between the cap interior and membrane.

In operation, when vacuum is generated (pulled) by the diaphragm pump 801, umbrella valve seals and duckbill valve 813 opens. Valve 817 closes at the minimum vacuum however, upon release of the vacuum stroke. Any excess air on the return stroke of the diaphragm is expelled through air vent created at hole 809.

Figure 21:
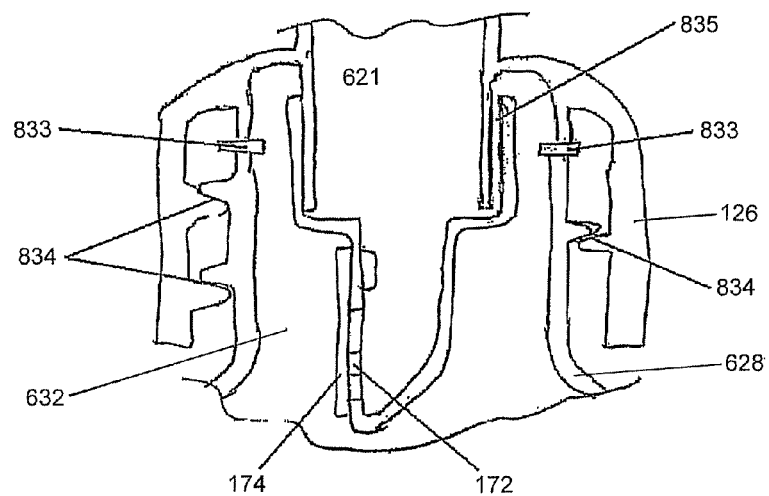
FIG. 21 is a cross section of the breast shield and collection bottle interface for a non-barrier system.

FIG. 21 shows a collection bottle and catch chamber valve assembly for use with the valving arranging described with respect to FIG. 20. Breast shield assembly catch chamber 621 connects the breast to the pump assembly in the usual fashion, as does the bottle 628 to the breastpump assembly collar (via screw threading 834 here). The collection bottle 628 is also shown using a sealing gasket 833, although this may be dispensed with given an adequate interference seal. Typical of some of the foregoing described assemblies, a valve 174 releasably seals against the surface of 172 to open and close the catch chamber. To control the pressure or vacuum in the collection bottle, an orifice passage 835 allows a small flow of air from the collection bottle into the breast pump conduit system. As the breast shield cycles to higher vacuum increasing the airflow through passage 835, this increases the vacuum in the collection bottle. The vacuum in the collection chamber 621 will be greater than the minimum control vacuum set by umbrella valve 817. The one way valve 174 will open to prevent vacuum in the breast shield from being less than the collection bottle. Expelled milk will be pushed through the valve 174, and the vacuum levels between the chamber 621 and the bottle will both finish the cycle and equalize, reaching the control vacuum set by umbrella valve 817.

Figure 22:
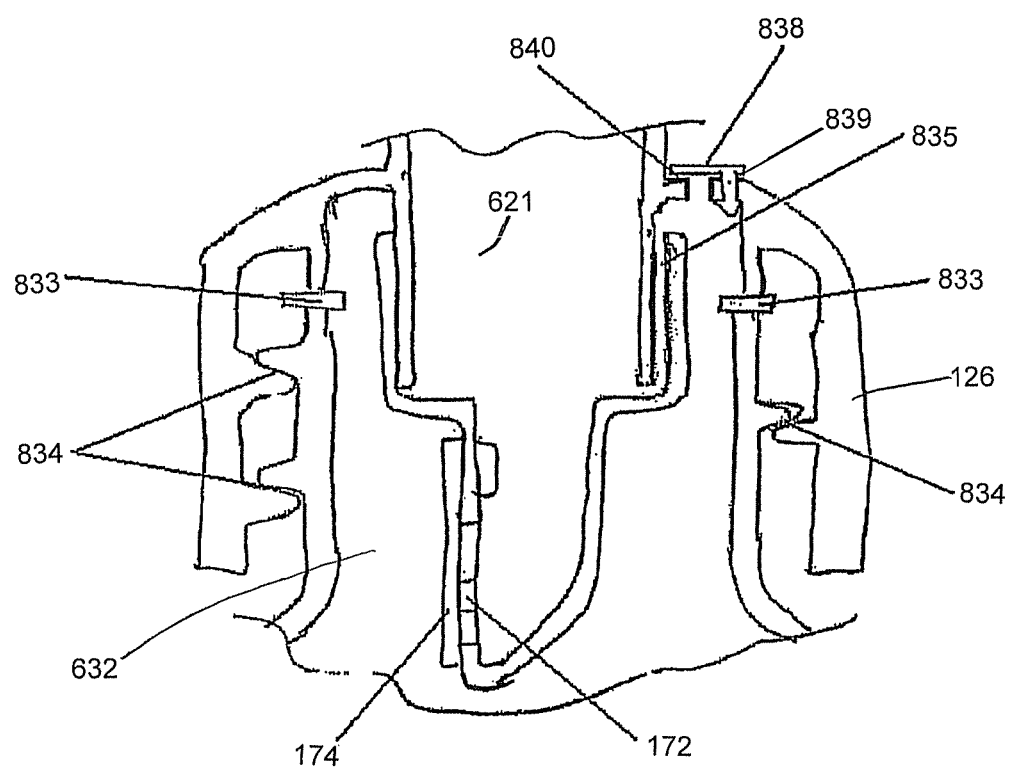
FIG. 22 is a variation of FIG. 21 for a barrier system.

FIG. 22 has all the features of FIG. 21, but further includes another valve 838. This is a one way reed valve 838 similar to that of 807 (but mounted using an integral pin or plug 839). The flap of the reed valve covers a hole or passage 840. Only when the control vacuum is set at or above atmospheric pressure will the one way valve 838 open to expel air.

It will be noted that in most of the foregoing embodiments (such as shown in FIGS. 1-5, 13, 14, 16-17, 20-22, and 23-27), the regulatory mechanism is separate from the vacuum pump. That is, it is external to the vacuum pump housing; or put another way, it is downstream from an output of the vacuum pump. This would be in an airline from the vacuum pump to the breastshield, for one example (such as shown in the embodiments of FIGS. 6 and 20), or on the breastshield assembly itself. These arrangements that are separate from the vacuum pump are to be contrasted with the embodiment of FIG. 18, where the regulation for a minimum vacuum is contained in the vacuum pump mechanism itself, and not exterior to (outside of) the vacuum pump.

Thus, while the invention has been described herein with relation to certain embodiments and applications, those with skill in this art will recognize changes, modifications, alterations and the like which still come within the spirit of the inventive concept, and such are intended to be included within the scope of the invention as expressed in the following claims.

What is claimed is:

1. An improved breastpump for the expression of mother's milk, the breastpump including a breastshield assembly and a vacuum pump located in a housing separated from the breastshield assembly and communicating with the breastshield assembly, comprising: a valving mechanism associated with a breastshield chamber in tubing to the breastshield assembly or in the breastshield assembly, and separate from the vacuum pump housing to maintain at least a minimum negative pressure within the breastshield chamber throughout at least some repeated cycles in a breastpumping session.

2. The improved breastpump of claim 1 wherein said breastpump is further adapted to manual operation.

3. The improved breastpump of claim 1 wherein said valving mechanism is further adapted to be operated in conjunction with a motor driven vacuum pump.

4. The improved breastpump of claim 1 wherein said minimum pressure is within a range of about −15 mmHg to −60 mmHg.

5. The improved breastpump of claim 1 wherein said mechanism is physically located on said breastshield as well as separate from the vacuum pump.

6. The improved breastpump of claim 1 wherein said mechanism is located remote from said breastshield as well as separate from the vacuum pump.

7. The improved breastpump of claim 1 wherein said minimum negative pressure establishes an amount of suction between the breast and said breastshield assembly capable of supporting said breastshield assembly in place on the breast.

8. The improved breastpump of claim 7 wherein said breastshield chamber has a plurality of suction channels along an interior surface of a breastshield funnel so as to provide an increased area of suction between said interior and the breast.

9. The improved breastpump of claim 8 further comprising a series of vacuum channels along said interior surface of the breastshield funnel, said vacuum channels interconnecting with said suction channels.

10. The improved breastpump of claim 9 wherein said suction channels are formed concentrically about a longitudinal axis of said breastshield funnel.

11. The improved breastpump of claim 10 wherein said suction channels are periodically broken along said interior surface of said breastshield funnel.

12. The improved breastpump of claim 7 wherein said minimum negative pressure is sufficient to support said breastshield assembly in place during milk expression without any other means of support required.

13. The improved breastpump of claim 1 wherein said valving mechanism is a simple one-way valve located in an airline in communication with said breastshield chamber, said valve having a biased opening operable to seal itself and thereby close said airline at a desired minimum negative pressure to thereby maintain said minimum negative pressure within said breastshield.

14. The improved breastpump of claim 13 further including an adjustable pressure regulator in said airline.

15. The improved breastpump of claim 14 wherein said pressure regulator is manually adjustable by a user.

16. The improved breastpump of claim 1 wherein said breastpump includes first and second airlines, the first airline communicating negative pressure for milk expression and the second airline in communication with said breastshield assembly which maintains said minimum negative pressure.

17. The improved breastpump of claim 1 wherein said valving mechanism comprises a flexible membrane mounted on a base extending across said airline, said base having at least one passage therethrough, said membrane having an aperture formed therethrough adapted to close and seal said base at said desired minimum negative pressure.

18. The improved breastpump of claim 1 wherein said valving mechanism comprises a flexible membrane, said membrane having a pin having disks at each end thereof and a dome defining a hole at an apex end of said dome through which the pin passes, said dome being formed on said flexible membrane, said dome biasing said pin in a manner to place one of said disks in sealing engagement with said dome base opening at a preset negative pressure within said vessel.

19. The improved breastpump of claim 18 wherein the dome further comprises a seal ring at the opposite end against which said one of said disks of the pin seats.

20. The improved breastpump of claim 19 wherein the dome is further provided with an opening to allow air to pass from one side of the dome to the other until said preset negative pressure is achieved.

21. The improved breastpump of claim 1 further comprising a pressure regulator having a duckbill valve which is one way toward the breastshield chamber and closable in communication with said vessel interior at a preset negative pressure within said vessel interior.

22. The improved breastpump of claim 21 wherein said second duckbill valve has a flow which is one way toward said vacuum pump.

23. An improved breastpump for the expression of mother's milk comprising a breastshield assembly, a vacuum pump located in a housing separated from the breastshield assembly, and a pneumatically operated one-way valve located in tubing to the breastshield assembly or in the breastshield assembly downstream from said vacuum pump housing communicating with a breastshield chamber to maintain at least a minimum negative pressure within said breastshield assembly throughout repeated cycles in a breastpumping session.

24. The improved breastpump of claim 23 wherein said breastpump is further adapted to manual operation.

25. The improved breastpump of claim 23 wherein said minimum negative pressure is a pressure within a range of about −15 mmHg to about −60 mmHg.

26. The improved breastpump of claim 23 wherein said breastshield assembly has a breast-receiving funnel portion including a nipple tunnel, the one-way valve being located within said nipple tunnel for controlling the flow of expressed milk from said breastshield assembly through a channel to a collection chamber.

27. The improved breastpump of claim 26 wherein said one-way valve comprises a base and a flexible membrane operatively engaged to said base.

28. The improved breastpump of claim 27 wherein said base is provided with at least one opening to allow flow of expressed milk therethrough.

29. The improved breastpump of claim 28 further comprising a pressure regulator.

30. The improved breastpump of claim 29 wherein said pressure regulator includes a manual adjustment device located in a pressure channel structure, said pressure channel structure communicating across opposite sides of said base.

31. The improved breastpump of claim 30 wherein said flexible membrane is located downstream on said base, said flexible membrane closing said base opening and sealing said base when a vacuum is present in said breastshield assembly upstream from said base which is relatively greater, or more negative, than the pressure downstream from said base.

32. The improved breastpump of claim 29 wherein said flexible membrane has an aperture formed therethrough for air passage and adapted to close and seal said base at a predetermined negative pressure within said breastshield assembly.

33. The improved breastpump of claim 32 wherein said aperture comprises two slits.

34. The improved breastpump of claim 29 wherein said pressure regulator includes a pin having disks at each end thereof and a dome defining a hole at an apex end of said dome through which said pin passes, said dome being formed on said flexible membrane, said dome biasing said pin in a manner to place one of said disks in sealing engagement with a dome base opening at a preset negative pressure within said breastshield assembly.

35. The improved breastpump of claim 34 wherein said dome further comprises a seal ring at said dome base opening against which said one of said disks of said pin seats.

36. The improved breastpump of claim 35 wherein said dome is further provided with an opening to allow air to pass from one side of said dome to the other until said preset negative pressure is achieved.

37. The improved breastpump of claim 29 wherein said pressure regulator comprises a duckbill valve which yields a one way flow toward said breastshield chamber and is closable in communication with said breastshield chamber at a predetermined negative pressure within said breastshield chamber.

38. The improved breastpump of claim 37, further including a second duckbill valve, said second duckbill valve being in communication with said breastshield chamber for milk and air flow, and yielding a one way flow toward said vacuum source.

39. The improved breastpump of claim 23 wherein said breastshield chamber has a plurality of suction channels along an interior surface of a breastshield funnel so as to provide an increased area of suction between said interior and the breast to support said breastshield in place on the breast.

40. The improved breastpump of claim 39 further comprising a series of vacuum channels along said interior surface of the breastshield funnel, said vacuum channels interconnecting with said suction channels.

41. The improved breastpump of claim 40 wherein said suction channels are formed concentrically about a longitudinal axis of said breastshield funnel.

42. The improved breastpump of claim 41 wherein said suction channels are periodically broken along said interior surface of said breastshield funnel.

43. The improved breastpump of claim 23 wherein said minimum negative pressure is sufficient to support said breastshield assembly in place during milk expression without any other means of support required.

44. A method for breastpumping comprising:
providing a breastshield assembly having a portion within which a woman's breast is capable of being received and within which a negative pressure can be generated to pull upon the breast;
supplying a source of negative pressure located within a housing in communication with said breastshield portion;
operating said source of negative pressure to repeatedly pull upon the breast; and
maintaining a minimum negative pressure within said breastshield portion throughout at least part of said operation of said source of negative pressure using a mechanism located in tubing to the breastshield assembly or in the breastshield assembly and separate from the housing of the source of negative pressure.

45. The method of claim 44 wherein said operating step comprises repeated cycles of increasing then decreasing vacuum, and said minimum negative pressure is maintained during at least some consecutive cycles.

46. The method of claim 45 wherein said minimum negative pressure level is varied between some cycles.

47. An improved breastpump for the expression of mother's milk comprising a breastshield assembly including a pressure-sensitive valve device associated with the breastshield assembly and located in tubing to the breastshield assembly or in the breastshield assembly and downstream to a housing containing a source of negative pressure that is remote from said breastshield assembly and connected thereto with a vacuum line, said valve device has cooperating elements which close at a minimum negative pressure that is maintained in repeated cycles in a breastpumping session.

48. The improved breastpump of claim 47 wherein the breastshield assembly has an interior portion within which a woman's breast is configured to be received and a first valve at an opposite end of said portion for controlling the flow of expressed milk from the breastshield assembly to a collection container and closing said interior portion.

49. The improved breastpump of claim 48 wherein the breastshield assembly is provided with a conduit structure which extends across said first valve, said conduit structure communicating between said breastshield interior portion and downstream of said first valve.

50. The improved breastpump of claim 49 wherein a pressure regulator is located within said conduit structure.

51. The improved breastpump of claim 50 further comprising a second valve which is said pressure regulator, said first and second valves each being one way valves.

52. The improved breastpump of claim 51 wherein each valve is of a duckbill type.

53. An improved method for operating a breastpump for the expression of mother's milk comprising operating a breastpump assembly to maintain a minimum vacuum level within a breastshield throughout at least some repeated cycles in a breastpumping session and also regulating pressure within a collection container to operate a valve controlling milk flow from a collection chamber downstream from said breastshield to said collection container, wherein said valve opens to release milk into said collection container by reduction in vacuum in said collection container to a level of vacuum about the same as or below that of said collection chamber, and to maintain the minimum vacuum level in the breastshield.

54. The improved method of claim 53, wherein the vacuum in said collection container operates to open said valve to milk flow when vacuum within said collection container exceeds said minimum vacuum maintained within said breastshield.

55. The improved method of claim 53, wherein said minimum vacuum level for said breastshield gradually increases in a manner to match an increasing vacuum in said collection container, until a desired upper bound to a vacuum level range is achieved.

56. An improved breastpump for the expression of mother's milk, comprising:
   a breastshield having an interior within which a woman's breast including the nipple is configured to be received,
   a mechanism communicating with said breastshield interior that maintains at least a minimum negative pressure within the breastshield throughout at least some consecutive cycles in a breastpumping session;
   a milk container communicating with said breastshield interior through a milk catch chamber intermediate said milk container and said breastshield, to receive milk therefrom;
   a source of vacuum communicating with said breastshield interior and said milk container, said source of vacuum being operated to generate negative pressure in said breastshield; and
   a valve structure between said milk container and said catch chamber, said valve structure including a first pneumatically operated valve capable of opening and closing for milk passage through use of a vacuum level in said milk container that is about the same as or less than that of said catch chamber and to maintain the minimum vacuum level in the breastshield.

57. The breastpump of claim 56 wherein said mechanism comprises a base and a flexible membrane operatively engaged to said base, said base is provided with at least one opening to allow flow of expressed milk therethrough, said flexible membrane is located downstream on said base, said flexible membrane closing said base opening and sealing said base when a vacuum is present in said breastshield upstream from said base which is relatively greater, or more negative, than the pressure downstream from said base, said flexible membrane having an aperture formed therethrough for air passage and adapted to close and seal said base at a predetermined negative pressure within said breastshield.

58. The improved breastpump of claim 57 wherein said aperture comprises two slits.

59. An apparatus for generating a minimum negative pressure over an area of the human body comprising:
   a pressure chamber having an interior and a perimeter sized to surround and be sealingly engaged with the area,
   an airline extending from the vessel interior to a source of negative pressure, and
   a valve mechanism communicating with the airline,
   the source of negative pressure being operated to generate repeated cycles of increasing and decreasing pressure,
   the valve mechanism comprising three cooperating one-way valves and being located adjacent said pressure chamber, said valve mechanism is adapted to close at a desired minimum negative pressure thereby closing the airline and maintaining a desired minimum negative pressure.

60. The apparatus of claim 59 wherein the three valves comprise an umbrella valve, and duckbill valve, and a reed valve.

61. The apparatus of claim 60 wherein the duckbill valve is located in between the umbrella valve and the reed valve.

62. The apparatus of claim 59 wherein said source of negative pressure is an expansible chamber device using an element that is moved relative to a chamber wall to generate a pressure change, one of said valves comprising an outlet to said chamber through which air in the chamber is expelled, the other two valves being a duckbill and umbrella valve combination, said duckbill valve allowing air flow in the direction of the expansible chamber device, said umbrella valve allowing air flow in the direction of the pressure chamber.

63. The apparatus of claim 59 wherein said pressure chamber is a breastshield of a breastpump.

64. The apparatus of claim 59 wherein said pressure chamber is a wound therapy device.

65. A breastpump for the expression of mother's milk comprising:
   a breastshield assembly;
   a vacuum pump located within a housing and providing a vacuum to the breastshield assembly; and
   a valving mechanism associated with a breastshield chamber in tubing to the breastshield assembly or in the breastshield assembly and separate from the vacuum pump housing to maintain at least a minimum negative pressure within the breastshield chamber throughout at least some repeated cycles in a breastpumping session, said valving mechanism having elements that are biased to close at a desired minimum negative pressure within the breastshield chamber.

* * * * *